United States Patent [19]

Klar et al.

[11] Patent Number: 5,716,989
[45] Date of Patent: Feb. 10, 1998

[54] BICYCLO[3.3.0]OCTANE DERIVATIVES, PROCESS FOR THEIR PRODUCTION AND THEIR PHARMACEUTICAL USE

[75] Inventors: Ulrich Klar; Hartmut Rehwinkel; Helmut Vorbruggen; Karl Heinz Thierauch; Peter Verhallen, all of Berlin, Germany

[73] Assignee: Schering Aktiengesellschaft, Berlin, Germany

[21] Appl. No.: 777,363

[22] Filed: Nov. 27, 1991

[30] Foreign Application Priority Data

Mar. 28, 1990 [DE] Germany ............... 40 10 355.2

[51] Int. Cl.⁶ ............................................. A61K 31/21
[52] U.S. Cl. .............. 514/510; 514/567; 562/439; 562/430; 560/34; 560/12; 560/13; 546/176; 546/329; 548/216; 548/253; 549/333; 549/357
[58] Field of Search ................... 562/439, 430; 560/34, 12, 13; 514/510, 567; 546/176, 329; 548/216, 253; 549/333, 357

[56] References Cited

U.S. PATENT DOCUMENTS

| 4,754,055 | 6/1988 | Djuric et al. | 560/116 |
|---|---|---|---|
| 5,028,733 | 7/1991 | Jones et al. | 560/119 |

FOREIGN PATENT DOCUMENTS

| 0011591 | 5/1980 | European Pat. Off. |
|---|---|---|
| 0231078 | 8/1987 | European Pat. Off. |
| 82-00142 | 1/1982 | WIPO |

Primary Examiner—Samuel Barts
Attorney, Agent, or Firm—Millen, White, Zelano & Branigan, P.C.

[57] ABSTRACT

The invention relates to bicyclo[3.3.0]octane compounds of formula I,

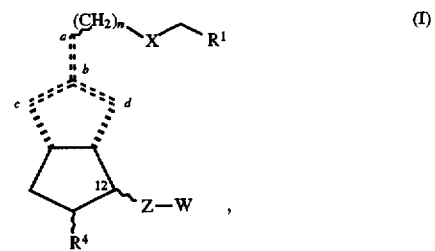

wherein the variable are defined in this specification, as well as their enantiomers, and their salts with physiologically compatible bases. α-, β-, or τ-Cyclodextrin clathrates of the compounds and the compounds encapsulated with liposomes are also included. The invention is further directed to processes for production of the compounds and their pharmaceutical use.

6 Claims, No Drawings

BICYCLO[3.3.0]OCTANE DERIVATIVES, PROCESS FOR THEIR PRODUCTION AND THEIR PHARMACEUTICAL USE

BACKGROUND OF THE INVENTION

The invention relates to bicyclo[3.3.0]octane derivatives, a process for their production as well as their use as auxiliary agents for pharmacological studies and as pharmaceutical agents.

Bicyclo[3.3.0]octane derivatives have been intensively dealt with in recent years, since carbacyclins derived from the bicyclo[3.3.0]octane system, such as, e.g., iloprost or cicaprost or other-analogoue isocarbacyclins, are biologically very potent and are also chemically and partially also metabolically stable prostacyclin-mimetic agents.

It has been found, surprisingly, that by the introduction of a nitrogen atom in the 13- or 14-position (prostaglandin numbering system) of the carbacyclin skeleton, chemically and metabolically stable carbacyclin analogs are obtained which are able to antagonize the pharmacological properties of unstable thromboxane $A_2$ ($TXA_2$) or $PGH_2$ as well as its stable analogs, such as, e.g., U46619 or U44069. Further, an additional agonistic active component comparable to the chemically and metabolically very unstable prostacyclin ($PGI_2$) can be introduced by the selection of the position or configuration of a double bond between the carbon atoms identified by a to d.

The compounds of this invention therefore constitute valuable auxiliary agents for selective treatment of diseases, which are attributable to a deficiency of endogenous $PGI_2$ and/or an excess of $TXA_2$ or $PGH_2$.

SUMMARY OF THE INVENTION

The invention relates to bicyclo[3.3.0]octane derivatives of formula I,

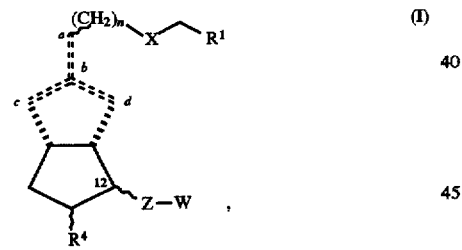

as well as their enantiomers, in which at most one double bond lies between the carbon atoms of centers a-b or b-c or b-d,

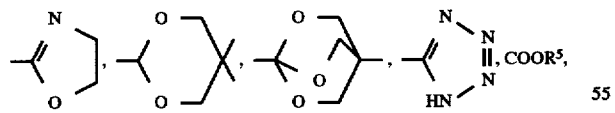

and $R^5$ can mean hydrogen or $C_1$–$C_{10}$ alkyl, $C_3$–$C_{10}$ cycloalkyl, $C_7$–$C_{16}$ aralkyl, optionally substituted by halogen, phenyl, $C_1$–$C_4$ alkoxy or di-($C_1$–$C_4$)-alkylamino, phenacyl or $C_6$–$C_{12}$ aryl substituted by Y or a 5- or 6-membered heterocyclic radical with at least one N, O or S atom, or -CONHR$^7$ with $R^7$ meaning hydrogen, $C_1$–$C_{10}$ alkanoyl or $C_1$–$C_{10}$ alkanesulfonyl, X means a $CH_2$ group or an O or S atom, n means 0–2, $R^4$ means a hydrogen atom, a free or functionally modified hydroxy group, and the OH group can be in α- or β-position, Z means

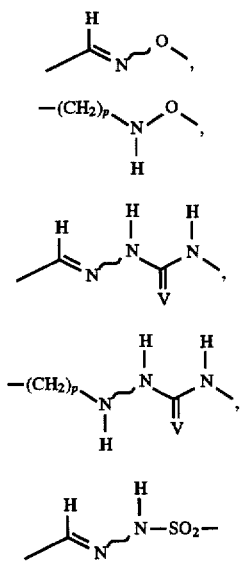

p means 0 or 1,

V means an O or S atom,

W means $C_1$–$C_{10}$ alkyl, $C_3$–$C_{10}$ cycloalkyl,

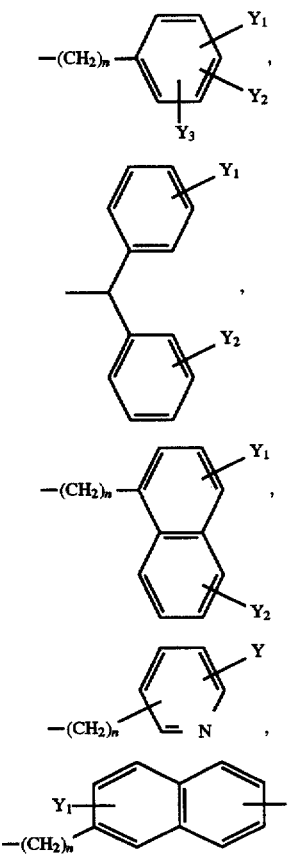

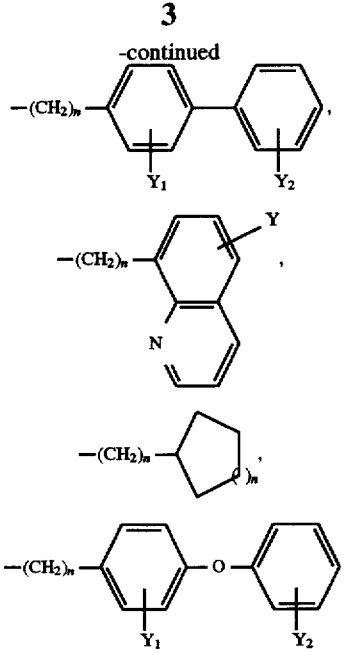

substituted by Y, $Y_1$, $Y_2$ and $Y_3$ are the same or different and mean Y, Y means hydrogen, halogen, $N_3$, $CF_3$, $OR^6$, $NO_2$, $COOR^6$ or $C_1$–$C_{10}$ alkyl, $R^6$ can be hydrogen, $C_1$–$C_{10}$ alkyl, $C_6$–$C_{12}$ aryl or $C_7$–$C_{16}$ aralkyl optionally substituted by halogen and, if $R^5$ means hydrogen, their salts with physiologically compatible bases, as well as the α-, β- or γ-cyclodextrin clathrates, as well as the compounds of formula I encapsulated with liposomes.

DESCRIPTION OF THE INVENTION

The definition of 5- or 6-membered heterocyclic radical relates to heterocycles, which contain at least one heteroatom, preferably nitrogen, oxygen or sulfur. For example, there can be mentioned 2-furyl, 3-furyl, 2-thienyl, 3-thienyl, 2-pyridyl, 3-pyridyl, 4-pyridyl.

As alkyl groups $R^5$, $R^6$, W and Y, straight-chain or branched-chain alkyl groups with 1–10 C atoms, such as, for example, methyl, ethyl, propyl, isopropyl, butyl, isobutyl, tert-butyl, pentyl, isopentyl, neopentyl, heptyl, hexyl, decyl, are suitable.

Alkyl groups $R^5$, $R^6$, W and Y can be substituted by halogen atoms, hydroxy groups, $C_1$–$C_4$ alkoxy groups, $C_6$–$C_{12}$ aryl groups, which can be substituted by halogen, di-($C_1$–$C_4$)-alkylamines and tri-($C_1$–$C_4$)-alkylammonium. Those alkyl groups which are singly substituted are preferred.

As substituents, for example, there can be mentioned fluorine, chlorine or bromine atoms, phenyl, dimethylamino, diethylamino, methoxy, ethoxy.

As preferred alkyl groups $R^5$, $R^6$, W and Y, those with 1–4 C atoms, such as, e.g., methyl, ethyl, propyl, isobutyl, butyl, can be mentioned.

As aryl groups $R^5$ and $R^6$, for example, phenyl, diphenyl, 1-naphthyl and 2-naphthyl, which can be substituted by 1–3 halogen atoms, a phenyl group, 1–3 alkyl groups each with 1–4 C atoms, a chloromethyl group, fluoromethyl group, carboxyl group, $C_1$–$C_4$ alkoxy group or hydroxy group, are suitable. The substitution in 3- and 4-position on the phenyl ring is preferred, for example, by fluorine, chlorine, $C_1$–$C_4$ alkoxy or trifluoromethyl or in 4-position by hydroxy.

Cycloalkyl groups $R^5$ and W can contain 3–10 carbon atoms, preferably 3–6 carbon atoms, in the ring. The rings can be substituted by alkyl groups with 1–4 carbon atoms. For example, there can be mentioned cyclopropyl, cyclobutyl, cyclopentyl, cyclohexyl, methylcyclopentyl, methylcyclohexyl.

The $C_7$–$C_{16}$ aralkyl groups in $R^1$ can contain 6 to 14 C atoms, preferably 6 to 10 C atoms (phenyl or naphthyl), in the ring, and 1 to 4 C atoms, preferably 1 to 2 C atoms, in the alkyl chain. Preferred aralkyl radicals are, e.g., benzyl, phenylethyl, 1-phenylethyl, 1-(2)-naphthylmethyl or 1-(2)-naphthylethyl.

The $C_1$–$C_{10}$ alkyl groups mentioned under the definitions should be straight-chain or branched alkyl groups, as they were already mentioned for the alkyl groups above.

The hydroxy groups in $R^4$ and W can be functionally modified, for example, by etherification or esterification, and the free or modified hydroxy groups in $R^4$ can be in α- or β-position, and free hydroxy groups are preferred.

As ether and acyl radicals, the radicals known to one skilled in the art are suitable. Easily cleavable ether radicals, such as, for example, the tetrahydropyranyl, tetrahydrofuranyl, tert-butyldimethylsilyl, tert-butyldiphenylsilyl, tribenzylsilyl radical, are preferred.

As acyl radicals, e.g., acetyl, propionyl, butyryl, benzoyl are suitable.

Halogen in the definitions for $R^5$, $R^6$ and Y means fluorine, chlorine, bromine and iodine.

Radicals "$C_1$–$C_{10}$ alkanoyl" or "$C_1$–$C_{10}$ alkanesulfonyl" for $R^7$ correspond to the already mentioned alkyl groups of the same length with the difference that they are bound on a carboxyl group. $C_1$–$C_4$ alkanoyl or $C_1$–$C_4$ alkanesulfonyl are preferred.

Inorganic and organic bases are suitable for salt formation with the free acids ($R^5$=H), as they are known to one skilled in the art for forming physiologically compatible salts. For example, there can be mentioned: alkali hydroxides, such as sodium hydroxide or potassium hydroxide, alkaline earth hydroxides, such as calcium hydroxide, ammonia, amines, such as ethanolamine, diethanolamine, triethanolamine, n-methylglucamine, morpholine, tris-(hydroxymethyl) methylamine, etc.

The compounds of formula I in which $R^1$ means the groups $COOR^5$, $R^4$ means hydrogen or hydroxyl, $R^5$ means hydrogen or methyl, $R^7$ means methanesulfonyl, X means oxygen or $CH_2$, n means 0 or 1, V means oxygen, are preferred.

The invention further relates to a process for the production of the compounds of formula I, which is characterized in that a compound of formula II

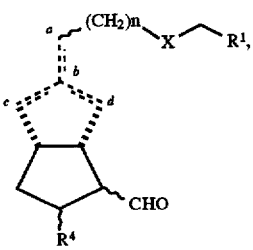

(II)

in which $R^1$ X, n, a-b, b-c b-d and $R^4$ have the above-indicated meanings and free OH groups in $R^4$ are protected, is reacted with compounds of formula

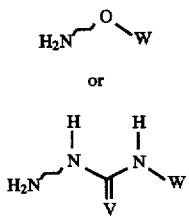

(or of the hydrochloride) or $H_2N—NH—SO_2—W$, in which V and W have the above-indicated meanings and free OH groups in W are protected, and optionally protected hydroxy groups in $R^4$ and W are released and/or free hydroxy groups are esterified, etherified and/or an esterified carboxy group is saponified or a carboxy group with a physiologically compatible base is converted to a salt or reacted to a clathrate with α-, β- or γ-cyclodextrin or encapsulated with liposomes.

The reaction of the compounds of general formula II to the compounds of general formula I is performed with the above-mentioned amino compounds in alcoholic solution (preferably ethanolic) in the presence of catalytic (equimolar) amounts of an organic base (e.g., pyridine, DBN, DBU, triethylamine, DMAP, etc.) at 20–100° C. (preferably 40–60° C.) within 2–24 hours (preferably 2–10 hours).

The release of functionally modified hydroxy groups $R^4$ and W takes place according to the methods known to one skilled in the art. For example, the cleavage of ether protecting groups is performed in an aqueous solution of an organic acid, such as, e.g., acetic acid, propionic acid, citric acid, i.a, or in an aqueous solution of an inorganic acid, such as, e.g., hydrochloric acid, or in the case of tetrahydropyranyl ethers with use of pyridinium-p-toluenesulfonate, preferably in alcohols as solvent or with use of anhydrous magnesium bromide, preferably in diethyl ether as solvent.

To improve the solubility, a water-miscible inert solvent is suitably added with use of aqueous-acid reaction conditions. Proven as suitable, there are, e.g., alcohols, such as methanol and ethanol, ethers, such as dimethoxyethane, dioxane and tetrahydrofuran, and tetrahydrofuran is preferably used.

The cleavage of silylether protecting groups takes place, for example, with tetrabutylammonium fluoride according to the methods known to one skilled in the art. As solvent, for example, tetrahydrofuran, diethyl ether, dioxane, methylene chloride, etc., are suitable. The cleavage is performed preferably at temperatures between 20° C. and 80° C.

The saponification of the acyl groups and carbacyclin esters is performed according to the methods known to one skilled in the art, such as, for example, with basic catalysts, such as, e.g., with alkali or alkaline-earth carbonates or hydroxides in an alcohol or the aqueous solution of an alcohol. As alcohols, aliphatic alcohols, such as, e.g., methanol, ethanol, butanol, etc., but preferably methanol, are suitable. As alkali carbonates and hydroxides, there can be mentioned lithium, sodium and potassium salts. The lithium and potassium salts are preferred. As alkaline-earth carbonates and hydroxides, for example, calcium carbonate, calcium hydroxide and barium carbonate are suitable. The reaction generally takes place at −10° C. to +70° C., but preferably at +25° C.

The introduction of the ester group $CO_2R^5$ for $R^1$ or $CO_2R^6$ for Y, in which $R^5$ or $R^6$ represents an alkyl group with 1–10 C atoms, takes place according to the methods known to one skilled in the art. The carboxy compounds ($R^5$=H or $R^6$=H) are reacted, for example, with diazohydrocarbons in a way known in the art. The esterification with diazohydrocarbons takes place, e.g., in that a solution of the diazohydrocarbon in an inert solvent, preferably in diethyl ether, is mixed with the carboxy compound, dissolved in the same or in another likewise inert solvent, such as, e.g., methylene chloride. After completion of the reaction within 1 to 60 minutes, the solvent is removed and the ester is purified in the usual way. Diazoalkanes are either known or can be produced according to known methods [Org. Reactions, Vol. 8, pages 389–394 (1954)].

The-introduction of the ester group $CO_2R^5$ for $R^1$ or $CO^2R^6$ for Y, in which $R^5$ or $R^6$ represents a substituted or unsubstituted aryl group, takes place according to the methods known to one skilled in the art. For example, the 1-carboxy compounds are reacted with the corresponding arylhydroxy compounds with dicyclohexylcarbodiimide in the presence of a suitable base, such as, e.g., pyridine, DMAP, triethylamine, in an inert solvent, such as, e.g., methylene chloride, ethylene chloride, chloroform, ethyl acetate, tetrahydrofuran, but preferably with chloroform. The reaction is performed at temperatures between −30° C. and +50° C., preferably at +10° C.

The carbacyclin derivatives of formula I with $R^5$ or $R^6$ meaning a hydrogen atom can be converted to salts with suitable amounts of the corresponding inorganic bases with neutralization. For example, by dissolving the corresponding acids in water, which contains stoichiometric amounts of the base, the solid inorganic salt is obtained after evaporation of the water or after addition of a water-miscible solvent, e.g., alcohol or acetone.

The production of the amine salts takes place in the usual way. For this purpose, the acid is dissolved in a suitable solvent, such as, e.g., ethanol, acetone, diethyl ether or benzene and 1 to 5 equivalents of the respective amine is added to this solution. In this case, the salt usually accumulates in solid form or is isolated in the usual way after evaporation of the solvent.

The functional modification of the free hydroxy groups takes place according to the methods known to one skilled in the art. For the introduction of the ether protecting groups, it is reacted, for example, with dihydropyran or methyl vinyl ether in methylene chloride or chloroform with use of catalytic amounts of an acid condensing agent, such as, e.g., p-toluenesulfonic acid. The respective enol ether is added in excess, preferably in 1.2 to 10 times the amount of the theoretical requirement. The reaction normally takes place at −10° C. to +30° C. and is completed after 2 to 45 minutes.

For the introduction of silylether protecting groups, it is reacted, for example, with t-butyl-diphenylchlorosilane or t-butyl-dimethylchlorosilane in dimethylformamide with use of a base, such as, e.g., imidazole. The respective silyl chloride is added in excess, preferably in 1.05 to 4 times the amount of the theoretical requirement. The reaction normally takes place at 0° C. to 30° C. and is completed after 1 to 24 hours.

The introduction of the acyl protecting groups takes place by a compound of formula I being reacted in a way known in the art with a carboxylic acid derivative, such as, e.g., acid chloride, acid anhydride, etc.

Biological Action and Area of Use of the New TXA$_2$ Antagonists

The compounds of this invention are suitable for treatment of diseases of the cardiovascular system, the stomach, the pancreas, the liver and the kidneys. They work in an antihypertensive and bronchodilatory manner. They are excellently suited for inhibition of the activation of platelets. Consequently, the new TXA$_2$ antagonists of formula I represent valuable pharmaceutical active ingredients. Moreover, the compounds are distinguished by the additional PGI$_2$-agonistic effectiveness which can be specifically applied and a broader spectrum of use caused in this way, by higher selectivity (in the absence of TXA$_2$ partial agonism), a substantially longer effectiveness and a greater stability as compared to similar TXA$_2$ antagonists.

The new TXA$_2$ antagonists have the properties typical for this family of compounds, such as, e.g., reduction of the peripheral-arterial, the coronary and pulmonary vascular resistance, reduction of the pulmonary blood pressure, reduction of the systemic blood pressure without reducing the cardiac output and coronary blood circulation at the same time, promotion of the kidney blood circulation and the blood circulation of other peripheral organs, increase of the cerebral blood circulation, inhibition of the platelet activation and dissolution of blood clots, inhibition of bronchoconstriction, inhibition of gastric acid secretion, cytoprotection of the heart, the stomach and intestinal mucous membrane, the liver, cytoprotection in the pancreas and in the kidneys as well as antiallergic properties. Therefore, the new TXA$_2$ antagonists are suitable on principle for treatment of stroke, prophylaxis and treatment of coronary heart diseases, for example, coronary thrombosis, for treatment of myocardial infarction, peripheral arteriopathies, for prophylaxis and treatment of other thromboembolic diseases and in arteriosclerosis, in ischemic attacks of the central nervous system and other disturbances of the blood circulation of the brain, for treatment of hypertonia and for treatment of diseases which accompany an increase of the pulmonary vascular resistance, such as, e.g., the pulmonary hypertonia, and for treatment of shock and asthma. They can further be used to inhibit labor pains and for treatment of toxicoses in pregnancies.

Further, the new TXA$_2$ antagonists can be used to improve the organ function after transplantation, for example, in kidney transplantation, to prevent rejection reactions, instead of heparin or as adjuvant in the case of dialysis or hemofiltration and in the case of storing dried blood plasma, for example, dried blood platelets.

The new TXA$_2$ antagonists have an antimetastatic action and antiproliferative properties. They are suitable on principle for treatment of hormone-dependent neoplasias.

The new TXA$_2$ antagonists can be used in combination with, for example, carbacyclins, prostacyclin and its analogs, 7-oxoprostacyclins, prostaglandins and their derivatives and 6-oxo-PGE$_1$- and 6-oxo-9-fluoroprastaglandin derivatives, with TXA$_2$-synthetase inhibitors, with phosphodiesterase inhibitors, with antagonists and receptor antagonists of various platelet stimulators (e.g., ADP, thrombin, collagen, PAF, adrenaline, serotonin, fibrinogen), with calcium antagonists, with fibrinolytic agents and thrombolytic agents, e.g., t-PA, with heparin and other anticoagulants, with cyclooxygenase inhibitors, e.g., acetylsalicylic acid, with inhibitors of lipoxygenases as well as antagonists of lipoxygenase products, with vasodilators, such as, e.g., nitro compounds, with antihypertensive agents, such as, e.g., beta-blockers or with diuretics.

The dose of the compounds is 0.1–500 mg/day, also in several partial doses, if they are administered to human patients. The unit dose for the pharmaceutically acceptable vehicle is 0.1–100 mg. For parenteral administration, sterile, injectable aqueous or oily solutions are used. For oral administration, for example, tablets, coated tablets, or capsules are suitable.

Thus, the invention also relates to pharmaceutical agents based on the compounds of general formula I and usual auxiliary agents and vehicles.

The active ingredients according to the invention are to be used in connection with the auxiliary agents known and usual in galenicals, e.g., for the production of antihypertensive agents.

The unit dose range for the ampoule is 0.1–100 mg, for the tablet 0.1–100 mg.

EXAMPLE 1

5-{(E)-(1S,5S,6S,7R)-7-Hydroxy-6-[(E/Z)-3-phenylureidoiminomethyl]-bicyclo[3.3.0]oct-3-ylidene}-pentanoic acid The colorless solution of 64 mg (160 micromol) of the compound, produced according to example 1a, in 4.5 ml of methanol is mixed with 1.8 ml of a 10% aqueous potassium hydroxide solution and allowed to stir for 16 hours at 23° C. By adding saturated citric acid solution, it is adjusted to a pH of 3–4, saturated with sodium chloride and extracted several times with a total of 20 ml of dichloromethane. The residue obtained after drying on magnesium sulfate, filtration and removal of the solvent is purified by chromatography on four analytic thin-layer slabs. A mixture of dichloromethane and methanol is used as mobile solvent, trichloromethane and ethanol are used as eluant. 35 mg (91 micromol, 57%) of the title compound is isolated as colorless oil.

IR (film): 3600–2500, 3380, 3340, 3090, 2940, 1710, 1670, 1595, 1540, 1450, 750 and 690 cm$^{-1}$.

EXAMPLE 1a

5-{(E)-(1S,5S,6S,7R)-7-Hydroxy-6-[(E/Z)-3-phenylureidoiminomethyl]-bicyclo[3.3.0]oct-3-ylidene}-pentanoic acid methyl ester 98 mg (202 micromol) of the compound produced according to example 1b is dissolved in 2.5 ml of anhydrous ethanol, mixed with 25 mg of pyridinium-p-toluenesulfonate and heated for 3 hours under an atmosphere of dry argon to 55° C. After cooling, it is mixed with a 50% sodium chloride solution and extracted several times with dichloromethane. The residue obtained after drying on magnesium sulfate, filtration and removal of the solvent is purified by chromatography on four analytic thin-layer slabs. A mixture of n-hexane and ethyl acetate is used as mobile solvent, ethyl acetate is used as eluant. 64 mg (160 micromol, 79%) of the title compound is isolated as colorless oil.

IR (film): 3500–3200, 3380, 3340, 3080, 2940, 1735, 1670, 1595, 1535, 1450, 750 and 690 cm$^{-1}$.

EXAMPLE 1b

5-{(E)-(1S,5S,6S,7R)-7-(Tetrahydropyran-2-yloxy)-6-[(E/Z)-3-phenylureidoiminomethyl]-bicyclo[3.3.0]oct-3-ylidene}-pentanoic acid methyl ester The solution of 88 mg (236 micromol) of the aldehyde, produced according to example 1c, in 2 ml of anhydrous ethanol is mixed with 48 mg of 4-phenylsemicarbazide, 2 drops of pyridine and heated for 3 hours under an atmosphere of dry argon to 55° C. The working up takes place as described in example 1a. After chromatography on about 30 ml of fine silica gel with use of a gradient system of n-hexane and ethyl acetate, 98 mg (202 micromol, 86%) of the title compound is isolated as colorless oil.

IR (film): 3400–3300, 2950, 2920, 2850, 1730, 1680, 1590, 1530, 1460, 1445 and 740 cm$^{-1}$.

EXAMPLE 1c

5-{(E)-(1S,5S,6R,7R)-7-(Tetrahydropyran-2-yloxy)-6-formyl-bicyclo[3.3.0]oct-3-ylidene}-pentanoic acid methyl ester The solution of 326 microliters of anhydrous dimethyl sulfoxide in 1.45 ml of dichloromethane is instilled in the solution of 179 microliters of freshly distilled oxalyl chloride in 3.6 ml of anhydrous dichloromethane under an atmosphere of dry argon at −60° C., stirred for another 15 minutes and mixed with the solution of 500 mg (1.42 mmol) of the alcohol, produced according to example 1d, in 2.88 ml of dichloromethane. It is allowed to react for 2.5 hours, quenched by adding 559 microliters of triethylamine, allowed to heat to 23° C., diluted with water, the organic phase is separated, and the aqueous phase is extracted several times with dichloromethane. The combined organic extracts are dried on magnesium sulfate and, after filtration and removal of the solvent, 500 mg (1.42 mmol, 100%) of the title compound is isolated as colorless oil, which is further reacted without purification.

EXAMPLE 1d

5-{(E)-(1S,5S,6S,7R)-7-(Tetrahydropyran-2-yloxy)-6-hydroxymethyl-bicyclo[3.3.0]oct-3-ylidene}-pentanoic acid methyl ester 9.18 g (15.5 mmol) of the ester produced according to example 1e is dissolved in 180 ml of anhydrous tetrahydrofuran, mixed with 37.3 ml of a 1M solution of tetrabutylammonium fluoride in tetrahydrofuran and stirred for 12 hours at 23° C. under an atmosphere of dry argon. It is poured in ice water, extracted several times with dichloromethane, the combined organic extracts are dried on magnesium sulfate and, after filtration and removal of the solvent, 11.3 g of crude oil is isolated which is separated by chromatography on about 400 ml of coarse silica gel with use of a gradient system of n-hexane and ethyl acetate. 3.94 g (11.2 mmol, 72%) of the title compound is isolated as colorless oil.

IR (film): 3600–3200, 2940, 2860, 1735, 1435, 1350, 1200, 1160, 1130, 1075, 1020, 975, 865 and 810 cm$^{-1}$.

EXAMPLE 1e

5-{(E)-(1S,5S,6S,7R)-7-(Tetrahydropyran-2-yloxy)-6-tert-butyldiphenylsilyloxymethyl-bicyclo[3.3.0]oct-3-ylidene}-pentanoic acid methyl ester The solution of 11.67 g (20.2 mmol) of polar acid A, produced according to example 1f, in 100 ml of dichloromethane is cooled to 3° C. and esterified by adding an ethereal solution of diazomethane. The residue obtained after removal of the solvent is purified by chromatography on about 500 ml of fine silica gel with use of an 8:2 mixture of n-hexane and ethyl acetate. 9.18 g (15.5 mmol, 77%) of the title compound is isolated as colorless oil.

IR (film): 3070, 3040, 2950, 2930, 2850, 1735, 1450, 1425, 1355, 1200, 1130, 1110, 1075, 1020, 865, 820, 740 and 700 cm$^{-1}$.

EXAMPLE 1f

5-{(E)-(1S,5S,6S,7R)-7-(Tetrahydropyran-2-yloxy)-6-tert-butyldiphenylsilyloxymethyl-bicyclo[3.3.0]oct-3-ylidene}-pentanoic acid (A) and 5-{(Z)-(1S,5S,6S,7R)-7-(tetrahydropyran-2-yloxy)-6-tert-butyldiphenylsilyloxymethyl-bicyclo[3.3.0]oct-3-ylidene}-pentanoic acid (B)

The emulsion of 117.5 g of carboxybutyltriphenylphosphonium bromide in a mixture of anhydrous dimethyl sulfoxide and tetrahydrofuran is cooled under an atmosphere of dry argon to 3° C. and mixed within 0.5 hour in portions with a total of 59.4 g of potassium-t-butanolate. It is stirred for another 0.5 hour and the solution of 21.75 g (44.1 mmol) of the ketone, produced according to example 1 g, in 40 ml of anhydrous tetrahydrofuran is instilled in the clear red solution within 10 minutes. It is heated for 1.5 hours to 35° C., poured on 1 l of ice water, adjusted to a pH of 4 by adding a saturated citric acid solution and extracted several times with diethyl ether. The combined organic extracts are washed with saturated sodium chloride solution, dried on magnesium sulfate and the residue obtained after filtration and removal of the solvent is purified by repeated chromatography on moderately fine silica gel with use of a gradient system of n-hexane and ethyl acetate. 11.67 g (20.2 mmol, 46%) of polar title compound A, as well as 7.44 g (12.9 mmol, 29%) of nonpolar title compound B are respectively isolated as colorless oil.

IR (film) of A and B: 3600–2500, 3070, 3050, 3010, 2940, 2850, 1705, 1425, 1355, 1200, 1125, 1110, 1075, 1020, 865, 815, 740 and 695 cm$^{-1}$.

EXAMPLE 1g (1S,2S,3R,5R)-3-(Tetrahydropyran-2-yloxy)-2-tert-butyldiphenylsilyloxymethyl-bicyclo[3.3.0]octan-7-one The solution of 25.77 g (63 mmol) of the alcohol, produced according to example 1h, in 250 ml of anhydrous dichloromethane is mixed with 6.71 ml of dihydropyran, 71 mg of p-toluenesulfonic acid chloride and allowed to react for 1.5 hours at 23° C. under an atmosphere of dry argon. It is washed neutral with a saturated sodium bicarbonate solution and saturated sodium chloride solution, dried on magnesium sulfate and the residue obtained after filtration and removal of the solvent is purified by chromatography on about 1 l of fine silica gel with use of a gradient system of n-hexane and ethyl acetate. 25.75 g (52.2 mmol, 83%) of the title compound is isolated as colorless oil.

IR (film): 3060, 3020, 2930, 2850, 1735, 1590, 1465, 1425, 1200, 1110, 1020, 970, 865, 820, 740 and 700 cm$^{-1}$.

EXAMPLE 1h (1S,2S,3R,5R)-3-Hydroxy-2-tert-butyldiphenylsilyloxymethyl-7,7-(2,2-dimethyltrimethylenedioxy)-bicyclo[3.3.0]octane 43.23 g (74.7 mmol) of the ketal produced according to example 1i is mixed with 1 l of a 65:35:10 mixture of acetic acid, water, tetrahydrofuran and stirred for 18 hours at 23° C. It is concentrated by evaporation and residual acetic acid is removed azeotropically by repeated addition of toluene.

The residue is purified by chromatography on 900 ml of fine silica gel with use of a gradient system of n-hexane and ethyl acetate. 22.65 g (55.4 mmol, 86%) of crystalline title compound in addition to 4.16 g (8.44 mmol, 13%) of the title compound from example 1g are isolated.

IR (CHCl$_3$): 3600–3200, 3070, 2940, 2850, 1730, 1590, 1465, 1425, 1400, 1255, 1110, 1040, 1005, 900, 860, 820 and 700 cm$^{-1}$.

EXAMPLE 1i (1S,2S,3R,5R)-3-(Tetrahydropyran-2-yloxy)-2-tert-butyldiphenylsilyloxymethyl-7,7-(2,2-dimethyltrimethylenedioxy)-bicyclo[3.3.0]octane 22.0 g (64.6 mmol) of the alcohol produced according to example 1j is dissolved in 200 ml of anhydrous dimethylformamide, mixed with 10 g of imidazole, 21 ml of tert-butyldiphenylchlorosilane and stirred for 14 hours at 23° C. under an atmosphere of dry argon. It is poured in 500 ml of ice water, which is covered with a layer of 300 ml of diethyl ether, the organic phase is separated, the aqueous phase is extracted several times with a total of 1.5 l of diethyl ether, the combined organic extracts are washed with water and saturated sodium chloride solution, dried on magnesium sulfate and the residue obtained after filtration and removal of the solvent is purified by chromatography on about 500 ml of fine silica gel with use of a gradient system of n-hexane and ethyl acetate. 36.6 g (63.2 mmol, 98%) of the title compound is isolated as solidified oil.

IR (CHCl$_3$): 3060, 3000, 2950, 2850, 1590, 1470, 1425, 1390, 1350, 1320, 1255, 1105, 1075, 1020, 910, 865, 820 and 700 cm$^{-1}$.

EXAMPLE 1j (1S,2S,3R,5R)-3-(Tetrahydropyran-2-yloxy)-7,7-(2,2-dimethyltrimethylenedioxy)-bicyclo[3.3.0]octane-2-methanol 24.3 g (66 mmol) of the ester produced according to example 1k is dissolved in 200 ml of anhydrous toluene, cooled under an atmosphere of dry argon to –20° C. and 55 ml of a 1.1M solution of diisobutylaluminum hydride in toluene is instilled within 30 minutes so that the inner temperature of –5° C. is not exceeded. It is allowed to react for another 30 minutes at –5° C., mixed with 12 ml of isopropanol and 11 ml of water, allowed to heat to 23° C. and stirred until a fine-grain precipitate results. After filtration and removal of the solvent, 22.06 g (64.8 mmol, 98%) of the title compound is isolated as crystalline solid.

IR (CHCl$_3$): 3600–3300, 2950, 2860, 1465, 1350, 1325, 1255, 1155, 1115, 1070, 1020, 975, 905, 865 and 810 cm$^{-1}$.

EXAMPLE 1k (1S,2S,3R,5R)-3-(Tetrahydropyran-2-yloxy)-7,7-(2,2-dimethyltrimethylenedioxy)-bicyclo[3.3.0]octane-2-carboxylic acid methyl ester 20.0 g (70.3 mmol) of (1S,2S,3R,5R)-3-hydroxy-7,7-(2,2-dimethyltrimethylenedioxy)-bicyclo[3.3.0]octane-2-carboxylic acid methyl ester is reacted analogously to example 1g and, after working up and purification, 24.8 g (67.3 mmol, 96%) of the title compound is isolated as crystalline solid.

IR (CHCl$_3$): 2950, 2860, 1725, 1435, 1255, 1165, 1115, 1075, 1030, 905, 865 and 815 cm$^{-1}$.

EXAMPLE 2

5-{(Z)-(1S,5S,6S,7R)-7-Hydroxy-6-[(E/Z)-3-phenylureidoiminomethyl]-bicyclo[3.3.0]oct-3-ylidene}-pentanoic acid 87 mg (218 micromol) of the ester produced according to example 2a is saponified analogously to example 1 and, after working up and purification, 36 mg (93 micromol, 43%) of the title compound is isolated as colorless oil.

IR (film): 3600–2500, 3370, 3220, 3100, 2950, 2930, 2850, 1710, 1680, 1595, 1540, 1450, 1235, 910, 755, 735 and 690 cm$^{-1}$.

EXAMPLE 2a

5-{(Z)-(1S,5S,6S,7R)-7-Hydroxy-6-[(E/Z)-3-phenylureidoiminomethyl]-bicyclo[3.3.0]oct-3-ylidene}-pentanoic acid methyl ester 113 mg (233 micromol) of the compound produced according to example 2b is reacted analogously to example 1a and, after working up and purification, 87 mg (218 micromol, 93%) of the title compound is isolated as colorless oil.

IR (film): 3500–3200, 3380, 3100, 2950, 2930, 2850, 1735, 1675, 1595, 1540, 1445, 1235, 910, 755, 735 and 690 cm$^{-1}$.

EXAMPLE 2b

5-{(Z)-(1S,5S,6S,7R)-7-(Tetrahydropyran-2-yloxy)-6-[(E/Z)-3-phenylureidoiminomethyl]-bicyclo[3.3.0]oct-3-ylidene}-pentanoic acid methyl ester 87 mg (248 micromol) of the aldehyde produced according to example 2c is reacted analogously to example 1b with use of 4-phenylsemicarbazide and, after working up and purification, 113 mg (233 micromol, 94%) of the title compound is isolated as colorless oil.

IR (film): 3400–3200, 2940, 2850, 1735, 1685, 1590, 1330, 1120, 1075, 1025, 970, 865, 815, 750 and 690 cm$^{-1}$.

EXAMPLE 2c

5-{(Z)-(1S,5S,6R,7R)-7-(Tetrahydropyran-2-yloxy)-6-formyl-bicyclo[3.3.0]oct-3-ylidene}-pentanoic acid methyl ester 500 mg (1.42 mmol) of the alcohol produced according to example 2d is oxidized analogously to example 1c and, after working up, 501 mg (1.42 mmol, 100%) of the title compound is isolated as colorless oil.

EXAMPLE 2d

5-{(Z)-(1S,5S,6S,7R)-7-(Tetrahydropyran-2-yloxy)-6-hydroxymethyl-bicyclo[3.3.0]oct-3-ylidene}-pentanoic acid methyl ester 7.16 g (12.1 mmol) of the compound produced according to example 2e is reacted analogously to example 1d and, after working up and purification, 3.35 g (9.5 mmol, 78%) of the title compound is isolated as colorless oil.

IR (film): 3600–3200, 2940, 2870, 1735, 1435, 1350, 1245, 1200, 1160, 1135, 1075, 1020, 975, 910, 865 and 810 cm$^{-1}$.

EXAMPLE 2e

5-{(Z)-(1S,5S,6S,7R)-7-(Tetrahydropyran-2-yloxy)-6-tert-butyldiphenylsilyloxymethyl-bicyclo[3.3.0]oct-3-ylidene}-pentanoic acid methyl ester 7.44 g (12.9 mmol) of more nonpolar acid B produced according to example 1f is esterified analogously to example 1e and, after working up and purification, 7.16 g (12.1 mmol, 94%) of the title compound is isolated as colorless oil.

IR (film): 3070, 3050, 2940, 2850, 1735, 1450, 1425, 1355, 1200, 1125, 1110, 1080, 1020, 865, 815, 740 and 700 cm$^{-1}$.

EXAMPLE 3

5-{(E)-(1S,5S,6S,7R)-7-Hydroxy-6-[(E/Z)-cyclohexylmethoxyiminomethyl]-bicyclo[3.3.0]oct-3-ylidene}-pentanoic acid 46 mg (122 micromol) of the ester produced according to example 3a is saponified analogously to example 1 and, after working up and purification, 31 mg (86 micromol, 70%) of the title compound is isolated as colorless oil.

IR (film): 3600–2500, 2920, 2850, 1710, 1450, 1385, 1080, 1040 and 1025 cm$^{-1}$.

EXAMPLE 3a

5-{(E)-(1S,5S,6S,7R)-7-Hydroxy-6-[(E/Z)-cyclohexylmethoxyiminomethyl]-bicyclo[3.3.0]oct-3-ylidene}-pentanoic acid methyl ester 70 mg (152 micromol) of the compound produced according to example 3b is reacted analogously to example 1a and, after working up and purification, 46 mg (122 micromol, 80%) of the title compound is isolated as colorless oil.

IR (film): 3500–3200, 2930, 2850, 1730, 1450, 1385, 1080, 1040 and 1025 cm$^{-1}$.

EXAMPLE 3b

5-{(E)-(1S,5S,6S,7R)-7-(Tetrahydropyran-2-yloxy)-6-[(E/Z)-cyclohexylmethoxyiminomethyl]-bicyclo[3.3.0]oct-3-ylidene}-pentanoic acid methyl ester 82 mg (234 micromol) of the aldehyde produced according to example 1c is reacted analogously to example 1b with use of cyclohexylmethoxyamine and, after working up and purification, 70 mg (152 micromol, 65%) of the title compound is isolated as colorless oil.

IR (film): 2940, 2850, 1735, 1450, 1380, 1080, 1040, 1025, 865 and 814 cm$^{-1}$.

EXAMPLE 4

5-{(Z)-(1S,5S,6S,7R)-7-Hydroxy-6-[(E/Z)-cyclohexylmethoxyiminomethyl]-bicyclo[3.3.0]oct-3-ylidene}-pentanoic acid 70 mg (186 micromol) of the ester produced according to example 4a is saponified analogously to example 1 and, after working up and purification, 56 mg (154 micromol, 83%) of the title compound is isolated as colorless oil.

IR (film): 3600–2500, 2930, 2850, 1710, 1450, 1080, 1035 and 1025 cm$^{-1}$.

EXAMPLE 4a

5-{(Z)-(1S,5S,6S,7R)-7-Hydroxy-6-[(E/Z)-cyclohexylmethoxyiminomethyl]-bicyclo[3.3.0]oct-3-ylidene}-pentanoic acid methyl ester 96 mg (214 micromol) of the compound produced according to example 4b is reacted analogously to example 1a and, after working up and purification, 70 mg (186 micromol, 87%) of the title compound is isolated as colorless oil.

IR (film): 3500–3200, 2930, 2850, 1735, 1450, 1080, 1035 and 1025 cm$^{-1}$.

EXAMPLE 4b

5-{(Z)-(1S,5S,6S,7R)-7-(Tetrahydropyran-2-yloxy)-6-[(E/Z)-cyclohexylmethoxyiminomethyl]-bicyclo[3.3.0]oct-3-ylidene}-pentanoic acid methyl ester 83 mg (236 micromol) of the aldehyde produced according to example 2c is reacted analogously to example 1b with use of cyclohexylmethoxyamine and, after working up and purification, 96 mg (214 micromol, 91%) of the title compound is isolated as colorless oil.

IR (film): 2940, 2850, 1735, 1445, 1080, 1035, 1025, 860 and 810 cm$^{-1}$.

EXAMPLE 5

5-{(E)-(1S,5S,6S,7R)-7-Hydroxy-6-[(E/Z)-4-trifluoromethylbenzyloxyiminomethyl]-bicyclo[3.3.0]oct-3-ylidene}-pentanoic acid 77 mg (175 micromol) of the ester produced according to example 5a is saponified analogously to example 1 and, after working up and purification, 67 mg (157 micromol, 90%) of the title compound is isolated as colorless oil.

IR (film): 3600–2500, 2930, 2870, 1710, 1620, 1325, 1165, 1125, 1065 and 1015 cm$^{-1}$.

EXAMPLE 5a

5-{(E)-(1S,5S,6S,7R)-7-Hydroxy-6-[(E/Z)-4-trifluoromethylbenzyloxyiminomethyl]-bicyclo[3.3.0]oct-3-ylidene}-pentanoic acid methyl ester 106 mg (202 micromol) of the compound produced according to example 5b is reacted analogously to example 1a and, after working up and purification, 77 mg (175 micromol, 87%) of the title compound is isolated as colorless oil.

IR (film): 3500–3200, 2930, 2860, 1735, 1620, 1325, 1165, 1125, 1065 and 1015 cm$^{-1}$.

EXAMPLE 5b

5-{(E)-(1S,5S,6S,7R)-7-(Tetrahydropyran-2-yloxy)-6-[(E/Z)-4-trifluoromethylbenzyloxyiminomethyl]-bicyclo[3.3.0]oct-3-ylidene}-pentanoic acid methyl ester 83 mg (236 micromol) of the aldehyde produced according to example 1c is reacted analogously to example 1b with use of 4-trifluoromethylphenylmethoxyamine and, after working up and purification, 106 mg (202 micromol, 86%) of the title compound is isolated as colorless oil.

IR (film): 2930, 2860, 1735, 1620, 1325, 1165, 1125, 1065, 1015, 865 and 820 cm$^{-1}$.

EXAMPLE 6

5-{(Z)-(1S,5S,6S,7R)-7-Hydroxy-6-[(E/Z)-4-trifluoromethylbenzyloxyiminomethyl]-bicyclo[3.3.0]oct-3-ylidene}-pentanoic acid 55 mg (126 micromol) of the ester produced according to example 6a is saponified analogously to example 1 and, after working up and purification, 51 mg (97 micromol, 77%) of the title compound is isolated as colorless oil.

IR (film): 3600–2400, 2940, 2870, 1710, 1620, 1420, 1325, 1165, 1125, 1065 and 1020 cm$^{-1}$.

EXAMPLE 6a

5-{(Z)-(1S,5S,6S,7R)-7-Hydroxy-6-[(E/Z)-4-trifluoromethylbenzyloxyiminomethyl]-bicyclo[3.3.0]oct-3-ylidene}-pentanoic acid methyl ester 96 mg (183 micromol) of the compound produced according to example 6b is reacted analogously to example 1a and, after working up and purification, 55 mg (126 micromol, 69%) of the title compound is isolated as colorless oil.

IR (film): 3500–3200, 2940, 2870, 1730, 1620, 1420, 1325, 1165, 1125, 1065 and 1020 $cm^{-1}$.

EXAMPLE 6b

5-{(Z)-(1S,5S,6S,7R)-7-(Tetrahydropyran-2-yloxy)-6-[(E/Z)-4-trifluoromethylbenzyloxyiminomethyl]-bicyclo[3.3.0]oct-3-ylidene}-pentanoic acid methyl ester 83 mg (236 micromol) of the aldehyde produced according to example 2c is reacted analogously to example 1b with use of 4-trifluoromethylphenylmethoxyamine and, after working up and purification, 96 mg (183 micromol, 78%) of the title compound is isolated as colorless oil.

IR (film): 2940, 2850, 1735, 1435, 1325, 1160, 1120, 1065, 1020, 865 and 815 $cm^{-1}$.

EXAMPLE 7

5-{(E)-(1S,5S,6S,7R)-7-Hydroxy-6-[(E/Z)-4-fluorobenzyloxyiminomethyl]-bicyclo[3.3.0]oct-3-ylidene}-pentanoic acid 69 mg (177 micromol) of the ester produced according to example 7a is saponified analogously to example 1 and, after working up and purification, 62 mg (165 micromol, 93%) of the title compound is isolated as colorless oil.

IR (film): 3600–2500, 3050, 2930, 2870, 1710, 1605, 1510, 1225, 1155, 1080, and 1025 $cm^{-1}$.

EXAMPLE 7a

5-{(E)-(1S,5S,6S,7R)-7-Hydroxy-6-[(E/Z)-4-fluorobenzyloxyiminomethyl]-bicyclo[3.3.0]oct-3-ylidene}-pentanoic acid methyl ester 90 mg (190 micromol) of the compound produced according to example 7b is reacted analogously to example 1a and, after working up and purification, 69 mg (177 micromol, 93%) of the title compound is isolated as colorless oil.

IR (film): 3500–3200, 3050, 2930, 2870, 1730, 1605, 1510, 1220, 1155, 1080 and 1025 $cm^{-1}$.

EXAMPLE 7b

5-{(E)-(1S,5S,6S,7R)-7-(Tetrahydropyran-2-yloxy)-6-[(E/Z)-4-fluorobenzyloxyiminomethyl]-bicyclo[3.3.0]oct-3-ylidene}-pentanoic acid methyl ester 83 mg (236 micromol) of the aldehyde produced according to example 1c is reacted analogously to example 1b with use of 4-fluorophenylmethoxyamine and, after working up and purification, 90 mg (190 micromol, 81%) of the title compound is isolated as colorless oil.

IR (film): 3050, 2940, 2870, 1735, 1605, 1510, 1220, 1155, 1080, 1025, 860 and 810 $cm^{-1}$.

EXAMPLE 8

5-{(Z)-(1S,5S,6S,7R)-7-Hydroxy-6-[(E/Z)-4-fluorobenzyloxyiminomethyl]-bicyclo[3.3.0]oct-3-ylidene}-pentanoic acid 63 mg (167 micromol) of the ester produced according to example 8a is saponified analogously to example 1 and, after working up and purification, 52 mg (139 micromol, 83%) of the title compound is isolated as colorless oil.

IR (film): 3600–2400, 3050, 2930, 2870, 1710, 1600, 1510, 1225, 1080, 1015 and 830 $cm^{-1}$.

EXAMPLE 8a

5-{(Z)-(1S,5S,6S,7R)-7-Hydroxy-6-[(E/Z)-4-fluorobenzyloxyiminomethyl]-bicyclo[3.3.0]oct-3-ylidene}-pentanoic acid methyl ester 85 mg (185 micromol) of the compound produced according to example 8b is reacted analogously to example 1a and, after working up and purification, 63 mg (167 micromol, 90%) of the title compound is isolated as colorless oil.

IR (film): 3500–3200, 3050, 2940, 2870, 1735, 1600, 1510, 1225, 1080, 1015 and 830 $cm^{-1}$.

EXAMPLE 8b

5-{(Z)-(1S,5S,6S,7R)-7-(Tetrahydropyran-2-yloxy)-6-[(E/Z)-4-fluorobenzyloxyiminomethyl]-bicyclo[3.3.0]oct-3-ylidene}-pentanoic acid methyl ester 83 mg (236 micromol) of the aldehyde produced according to example 2c is reacted analogously to example 1b with use of 4-fluorophenylmethoxyamine and, after working up and purification, 85 mg (185 micromol, 78%) of the title compound is isolated as colorless oil.

IR (film): 3040, 2940, 2860, 1735, 1600, 1510, 1435, 1355, 1220, 1155, 1120, 1075, 1030, 1020, 870 and 820 $cm^{-1}$.

EXAMPLE 9

5-{(E)-(1S,5S,6S,7R)-7-Hydroxy-6-[(E/Z)-benzyloxyiminomethyl]-bicyclo[3.3.0]oct-3-ylidene}-pentanoic acid 52 mg (140 micromol) of the ester produced according to example 9a is saponified analogously to example 1 and, after working up and purification, 49 mg (137 micromol, 98%) of the title compound is isolated as colorless oil.

IR (film): 3600–2500, 3030, 2930, 2870, 1705, 1455, 1385, 1240, 1080, 1020 and 700 $cm^{-1}$.

EXAMPLE 9a

5-{(E)-(1S,5S,6S,7R)-7-Hydroxy-6-[(E/Z)-benzyloxyiminomethyl]-bicyclo[3.3.0]oct-3-ylidene}-pentanoic acid methyl ester 79 mg (173 micromol) of the compound produced according to example 9b is reacted analogously to example 1a and, after working up and purification, 52 mg (140 micromol, 81%) of the title compound is isolated as colorless oil.

IR (film): 3500–3200, 3030, 2930, 2870, 1730, 1455, 1380, 1240, 1080, 1020 and 700 $cm^{-1}$.

EXAMPLE 9b

5-{(E)-(1S,5S,6S,7R)-7-(Tetrahydropyran-2-yloxy)-6-[(E/Z)-benzyloxyiminomethyl]-bicyclo[3.3.0]oct-3-ylidene}-pentanoic acid methyl ester 83 mg (236 micromol) of the aldehyde produced according to example 1c is reacted analogously to example 1b with use of phenylmethoxyamine and, after working up and purification, 79 mg (173 micromol, 73%) of the title compound is isolated as colorless oil.

IR (film): 3040, 2930, 2870, 1735, 1455, 1380, 1240, 1080, 1020, 865, 815 and 700 cm$^{-1}$.

EXAMPLE 10

5-{(Z)-(1S,5S,6S,7R)-7-Hydroxy-6-[(E/Z)-benzyloxyiminomethyl]-bicyclo[3.3.0]oct-3-ylidene}-pentanoic acid 60 mg (167 micromol) of the ester produced according to example 10a is saponified analogously to example 1 and, after working up and purification, 54 mg (151 micromol, 90%) of the title compound is isolated as colorless oil.

IR (film): 3600–2400, 3060, 3030, 2930, 2870, 1705, 1505, 1245, 1080, 1015, 920 and 695 cm$^{-1}$.

EXAMPLE 10a

5-{(Z)-(1S,5S,6S,7R)-7-Hydroxy-6-[(E/Z)-benzyloxyiminomethyl]-bicyclo[3.3.0]oct-3-ylidene}-pentanoic acid methyl ester 79 mg (178 micromol) of the compound produced according to example 10b is reacted analogously to example 1a and, after working up and purification, 60 mg (167 micromol, 94%) of the title compound is isolated as colorless oil.

IR (film): 3500–3200, 3050, 3030, 2930, 2870, 1735, 1505, 1240, 1080, 1015, 920 and 695 cm$^{-1}$.

EXAMPLE 10b

5-{(Z)-(1S,5S,6S,7R)-7-(Tetrahydropyran-2-yloxy)-6-[(E/Z)-benzyloxyiminomethyl]-bicyclo[3.3.0]oct-3-ylidene}-pentanoic acid methyl ester 83 mg (236 micromol) of the aldehyde produced according to example 2c is reacted analogously to example 1b with use of phenylmethoxyamine and, after working up and purification, 79 mg (178 micromol, 75%) of the title compound is isolated as colorless oil.

IR (film): 3040, 2940, 2850, 1735, 1450, 1435, 1355, 1200, 1120, 1075, 1035, 1020, 970, 910, 865, 815 and 695 cm$^{-1}$.

EXAMPLE 11

5-{(E)-(1S,5S,6S,7R)-7-Hydroxy-6-[(E/Z)-1-naphthylmethoxyiminomethyl]-bicyclo[3.3.0]oct-3-ylidene}-pentanoic acid 80 mg (190 micromol) of the ester produced according to example 11a is saponified analogously to example 1 and, after working up and purification, 71 mg (174 micromol, 92%) of the title compound is isolated as colorless oil.

IR (film): 3600–2400, 3050, 2930, 1705, 1600, 1430, 1385, 1240, 1165, 1080, 1020, 915, 800, 790 and 775 cm$^{-1}$.

EXAMPLE 11a

5-{(E)-(1S,5S,6S,7R)-7-Hydroxy-6-[(E/Z)-1-naphthylmethoxyiminomethyl]-bicyclo[3.3.0]oct-3-ylidene}-pentanoic acid methyl ester 109 mg (216 micromol) of the compound produced according to example 11b is reacted analogously to example 1a and, after working up and purification, 80 mg (190 micromol, 88%) of the title compound is isolated as colorless oil.

IR (film): 3500–3200, 3050, 2930, 2860, 1735, 1600, 1425, 1385, 1240, 1165, 1080, 1020, 915, 805, 790 and 775 cm$^{-1}$.

EXAMPLE 11b

5-{(E)-(1S,5S,6S,7R)-7-(Tetrahydropyran-2-yloxy)-6-[(E/Z)-1-naphthylmethoxyiminomethyl]-bicyclo[3.3.0]oct-3-ylidene}-pentanoic acid methyl ester 33 mg (236 micromol) of the aldehyde produced according to example 1c is reacted analogously to example 1b with use of 1-naphthylmethoxyamine and, after working up and purification, 109 mg (216 micromol, 92%) of the title compound is isolated as colorless oil.

IR (film): 3040, 2940, 2850, 1735, 1595, 1450, 1435, 1350, 1200, 1160, 1120, 1075, 1030, 1020, 970, 910, 865, 820, 790 and 725 cm$^{-1}$.

EXAMPLE 12

5-{(Z)-(1S,5S,6S,7R)-7-Hydroxy-6-[(E/Z)-1-naphthylmethoxyiminomethyl]-bicyclo[3.3.0]oct-3-ylidene}-pentanoic acid 57 mg (135 micromol) of the ester produced according to example 12a is saponified analogously to example 1 and, after working up and purification, 54 mg (132 micromol, 98%) of the title compound is isolated as colorless oil.

IR (film): 3600–2500, 3050, 2940, 1705, 1600, 1240, 1080, 1000, 915, 800, 790 and 780 cm$^{-1}$.

EXAMPLE 12a

5-{(Z)-(1S,5S,6S,7R)-7-Hydroxy-6-[(E/Z)-1-naphthylmethoxyiminomethyl]-bicyclo[3.3.0]oct-3-ylidene}-pentanoic acid methyl ester 97 mg (192 micromol) of the compound produced according to example 12b is reacted analogously to example 1a and, after working up and purification, 57 mg (135 micromol, 70%) of the title compound is isolated as colorless oil.

IR (film): 3500–3200, 3040, 2950, 1735, 1595, 1240, 1080, 995, 915, 800, 790 and 780 cm$^{-1}$.

EXAMPLE 12b

5-{(Z)-(1S,5S,6S,7R)-7-(Tetrahydropyran-2-yloxy)-6-[(E/Z)-1-naphthylmethoxyiminomethyl]-bicyclo[3.3.0]oct-3-ylidene}-pentanoic acid methyl ester 83 mg (236 micromol) of the aldehyde produced according to example 2d is reacted analogously to example 1b with use of 1-naphthylmethoxyamine and, after working up and purification, 97 mg (192 micromol, 82%) of the title compound is isolated as colorless oil.

IR (film): 3040, 2960, 1735, 1600, 1235, 1080, 1000, 915, 865, 815, 800, 790 and 780 cm$^{-1}$.

EXAMPLE 13

5-{(E)-(1S,5S,6S,7R)-7-Hydroxy-6-[(E/Z)-diphenylmethoxyiminomethyl]-bicyclo[3.3.0]oct-3-ylidene}-pentanoic acid 69 mg (154 micromol) of the ester produced according to example 13a is saponified analogously to example 1 and, after working up and purification, 48 mg (110 micromol, 71%) of the title compound is isolated as colorless oil.

IR (film): 3600–2400, 3080, 3030, 2930, 2860, 1705, 1600, 1495, 1455, 1300, 1245, 1185, 1080, 1020, 935, 915, 745 and 700 cm$^{-1}$.

EXAMPLE 13a

5-{(E)-(1S,5S,6S,7R)-7-Hydroxy-6-[(E/Z)-diphenylmethoxyiminomethyl]-bicyclo[3.3.0]oct-3-ylidene}-pentanoic acid methyl ester 100 mg (188 micromol) of the compound produced according to example 13b is reacted analogously to example 1a and, after working up and purification, 69 mg (154 micromol, 82%) of the title compound is isolated as colorless oil.

IR (film): 3500–3200, 3080, 3030, 2940, 2870, 1730, 1600, 1495, 1455, 1300, 1245, 1185, 1075, 1020, 935, 915, 745 and 700 cm$^{-1}$.

EXAMPLE 13b

5-{(E)-(1S,5S,6S,7R)-7-(Tetrahydropyran-2-yloxy)-6-[(E/Z)-diphenylmethoxyiminomethyl]-bicyclo[3.3.0]oct-3-ylidene}-pentanoic acid methyl ester 82 mg (234 micromol) of the aldehyde produced according to example 1d is reacted analogously to example 1b with use of diphenylmethoxyamine and, after working up and purification, 109 mg (205 micromol, 88%) of the title compound is isolated as colorless oil.

IR (film): 3080, 3030, 2940, 2870, 1735, 1600, 1495, 1450, 1300, 1245, 1185, 1080, 1020, 935, 915, 865, 815, 745 and 700 cm$^{-1}$.

EXAMPLE 14

5-{(Z)-(1S,5S,6S,7R)-7-Hydroxy-6-[(E/Z)-diphenylmethoxyiminomethyl]-bicyclo[3.3.0]oct-3-ylidene}-pentanoic acid 147 mg (328 micromol) of the ester produced according to example 14a is saponified analogously to example 1 and, after working up and purification, 98 mg (226 micromol, 69%) of the title compound is isolated as colorless oil.

IR (film): 3600–2400, 3070, 3040, 2940, 1710, 1600, 1495, 1455, 1265, 1245, 1175, 1080, 1020, 935, 920, 745 and 700 cm$^{-1}$.

EXAMPLE 14a

5-{(Z)-(1S,5S,6S,7R)-7-Hydroxy-6-[(E/Z)-diphenylmethoxyiminomethyl]-bicyclo[3.3.0]oct-3-ylidene}-pentanoic acid methyl ester 209 mg (393 micromol) of the compound produced according to example 14b is reacted analogously to example 1a and, after working up and purification, 147 mg (328 micromol, 84%) of the title compound is isolated as colorless oil.

IR (film): 3500–3200, 3070, 3040, 2940, 1735, 1600, 1495, 1455, 1265, 1245, 1175, 1080, 1020, 935, 920, 745 and 700 cm$^{-1}$.

EXAMPLE 14b

5-{(Z)-(1S,5S,6S,7R)-7-(Tetrahydropyran-2-yloxy)-6-[(E/Z)-diphenylmethoxyiminomethyl]-bicyclo[3.3.0]oct-3-ylidene}-pentanoic acid methyl ester 345 mg (984 micromol) of the aldehyde produced according to example 2d is reacted analogously to example 1b with use of diphenylmethoxyamine and, after working up and purification, 426 mg (801 micromol, 81%) of the title compound is isolated as colorless oil.

IR (film): 3070, 3050, 2940, 2870, 1735, 1600, 1495, 1450, 1265, 1245, 1175, 1080, 1020, 935, 920, 865, 820, 745 and 695 cm$^{-1}$.

EXAMPLE 15

5-{((E)-1S,5S,6S,7R)-7-Hydroxy-6-[(E/Z)-3-(3-chlorophenyl)-ureidoiminomethyl]-bicyclo[3.3.0]oct-3-ylidene}-pentanoic acid 50 mg (115 micromol) of the compound produced according to example 15a is saponified analogously to example 1 and, after working up and purification, 25 mg (60 micromol, 52%) of the title compound is isolated as crystalline solid.

$^{1}$H-NMR (CD$_3$OD): δ=1.2–1.32(m, 1H), 1.6–1.74(m, 2H), 2.0–2.6 (m, 13H), 3.9–4.04 (m, 1H), 5.27–5.37 (m, 1H), 7.02 (m, 1H), 7.2(d,1H), 7.25(d,1H), 7.38(m,1H), 7.7(m, 1H).

EXAMPLE 15a

5-{((E)-1S,5S,6S,7R)-7-Hydroxy-6-[(E/Z)-3-(3-chlorophenyl)-ureidoiminomethyl]-bicyclo[3.3.0]oct-3-ylidene}-pentanoic acid methyl ester 81 mg (232 micromol) of the compound produced according to example 1c is reacted analogously to example 1a with use of 4-(3-chlorophenyl)-semicarbazide hydrochloride and, after working up and purification, 50 mg (115 micromol, 50%) of the title compound is isolated as colorless oil.

IR (film): 3600–3000, 3360, 3110, 2940, 1735, 1690, 1590, 1530, 1480, 1425, 1305, 1225, 1095, 1015, 875, 775, 740 and 680 cm$^{-1}$.

EXAMPLE 16

5-{((Z)-1S,5S,6S,7R)-7-Hydroxy-6-[(E/Z)-3-(3-chlorophenyl)-ureidoiminomethyl]-bicyclo[3.3.0]oct-3-ylidene}-pentanoic acid 59 mg (136 micromol) of the compound produced according to example 16a is saponified analogously to example 1 and, after working up and purification, 53 mg (125 micromol, 92%) of the title compound is isolated as colorless solid.

IR (KBr): 3600–2400, 3360, 3230, 2940, 1700, 1590, 1530, 1425, 1310, 1230, 1090, 1010, 870, 775 and 680 cm$^{-1}$.

EXAMPLE 16a

5-{((Z)-1S,5S,6S,7R)-7-Hydroxy-6-[(E/Z)-3-(3-chlorophenyl)-ureidoiminomethyl]-bicyclo[3.3.0]oct-3-ylidene}-pentanoic acid methyl ester 100 mg (226 micromol) of the compound produced according to example 2c is reacted analogously to example 1b with use of 4-(2-chlorophenyl)-semicarbazide hydrochloride and, after working up and purification, 59 mg (136 micromol, 60%) of the title compound is isolated as colorless oil.

IR (film): 3600–3000, 3360, 3110, 2940, 1730, 1690, 1585, 1530, 1480, 1425, 1305, 1225, 1095, 1010, 875, 775, 740 and 680 cm$^{-1}$.

EXAMPLE 17

5-{((E)-1S,5S,6S,7R)-7-Hydroxy-6-[(E/Z)-3-(3,4-dichlorophenyl)-ureidoiminomethyl]-bicyclo[3.3.0]oct-3-ylidene}-pentanoic acid 26 mg (55 micromol) of the compound produced according to example 17a is saponified analogously to example 1 and, after working up and purification, 10 mg (22 micromol, 40%) of the title compound is isolated as crystalline solid.

$^1$H-NMR (CD$_3$OD): δ=1.2–1.34(m, 1H), 1.6–1.74(m, 2H), 1.96–2.6(m,13H), 3.9–7.87 (m, 1H).

EXAMPLE 17a

5-{((E)-1S,5S,6S,7R)-7-Hydroxy-6-[(E/Z)-3-(3,4-dichlorophenyl)-ureidoiminomethyl]-bicyclo[3.3.0]oct-3-ylidene}-pentanoic acid methyl ester 81 mg (232 micromol) of the compound produced according to example 1c is reacted analogously to example 1b with use of 4-(3,3-dichlorophenyl)-semicarbazide hydrochloride and, after working up and purification, 26 mg (55 micromol, 24%) of the title compound is isolated as colorless oil.

IR (film): 3600–3000, 3360, 3120, 2940, 1730, 1690, 1580, 1520, 1470, 1390, 1160, 1110, 1025, 865, 825, 770 and 740 cm$^{-1}$.

EXAMPLE 18

5-{((Z)-1S,5S,6S,7R)-7-Hydroxy-6-[(E/Z)-3-(3,4-dichlorophenyl)-ureidoiminomethyl]-bicyclo[3.3.0]oct-3-ylidene}-pentanoic acid 64 mg (137 micromol) of the compound produced according to example 18a is saponified analogously to example 1 and, after working up and purification, 48 mg (105 micromol, 77%) of the title compound is isolated as colorless solid.

IR (KBr): 3600–2400, 3360, 3330, 2940, 1700, 1580, 1525, 1470, 1395, 1310, 1225, 1130, 1030, 870, 815 and 750 cm$^{-1}$.

EXAMPLE 18a

5-{((Z)-1S,5S,6S,7R)-7-Hydroxy-6-[(E/Z)-3-(3,4-dichlorophenyl)-ureidoiminomethyl]-bicyclo[3-3-O]oct-3-ylidene}-pentanoic acid methyl ester 100 mg (226 micromol) of the compound produced according to example 2c is reacted analogously to example 1b with use of 4-(3,4-dichlorophenyl)-semicarbazide hydrochloride and, after working up and purification, (mg micromol, %) of the title compound is isolated as colorless oil.

IR (film): 3600–3000, 3360, 3200, 3120, 2940, 1730, 1690, 1580, 1520, 1470, 1390, 1160, 1120, 1025, 865, 825, 770 and 740 cm$^{-1}$.

EXAMPLE 19

5-{((E)-1S,5S,6S,7R)-7-Hydroxy-6-[(E/Z)-3-(4-chlorophenyl)-ureidoiminomethyl]-bicyclo[3.3.0]oct-3-ylidene}-pentanoic acid 30 mg (63 micromol) of the compound produced according to example 19a is saponified analogously to example 1 and, after working up and purification, 12 mg (29 micromol, 45%) of the title compound is isolated as crystalline solid.

$^1$H-NMR (CD$_3$OD): δ=1.2–1.32(m,1H), 1.58–1.74(m, 2H), 1.96–2.6 (m, 13H), 3.9–4.05 (m, 1H) , 5.32 (m, 1H), 7.17–7.3 (m, 3H), 7.5(d,2H).

EXAMPLE 19a

5-{((E)-1S,5S,6S,7R)-7-Hydroxy-6-[(E/Z)-3-(4-chlorophenyl)-ureidoiminomethyl]-bicyclo[3.3.0]oct-3-ylidene}-pentanoic acid methyl ester 81 mg (232 micromol) of the compound produced according to example 1c is reacted analogously to example 1b with use of 4-(4-chlorophenyl)-semicarbazide hydrochloride and, after working up and purification, 30 mg (63 micromol, 27%) of the title compound is isolated as colorless oil.

IR (film): 3600–3000, 3350, 3220, 2940, 1730, 1680, 1590, 1530, 1490, 1400, 1310, 1225, 1090, 825 and 735 cm$^{-1}$.

EXAMPLE 20

5-{((Z)-1S,5S,6S,7R)-7-Hydroxy-6-[(E/Z)-3-(4-chlorophenyl)-ureidoiminomethyl]-bicyclo[3.3.0]oct-3-ylidene}-pentanoic acid 61 mg (141 micromol) of the compound produced according to example 20a is saponified analogously to example 1 and, after working up and purification, 51 mg (122 micromol, 87%) of the title compound is isolated as colorless solid.

IR (KBr): 3600–2400, 3360, 3240, 2940, 1700, 1590, 1530, 1490, 1405, 1310, 1230, 1090, 1010, 820 and 750 cm$^{-1}$.

EXAMPLE 20a

5-{((Z)-1S,5S,6S,7R)-7-Hydroxy-6-[(E/Z)-3-(4-chlorophenyl)-ureidoiminomethyl]-bicyclo[3.3.0]oct-3-ylidene}-pentanoic acid methyl ester 100 mg (226 micromol) of the compound produced according to example 2c is reacted analogously to example 1b with use of 4-(4-chlorophenyl)-semicarbazide hydrochloride and, after working up and purification, 61 mg (141 micromol, 62%) of the title compound is isolated as colorless oil.

IR (film): 3600–3000, 3360, 3210, 2940, 1730, 1680, 1590, 1530, 1490, 1400, 1310, 1230, 1090, 825 and 735 cm$^{-1}$.

EXAMPLE 21

5-{((E)1S,5S,6S,7R)-7-Hydroxy-6-[(E/Z)-3-(4-nitrophenyl)-ureidoiminomethyl]-bicyclo[3.3.0]oct-3-ylidene}-pentanoic acid 21 mg (47 micromol) of the compound produced according to example 21a is saponified analogously to example 1 and, after working up and purification, 6 mg (14 micromol, 30%) of the title compound is isolated as crystalline solid.

$^1$H-NMR (CD$_3$OD): δ=1.2–1.32(m, 1H), 1.62–1.74(m, 2H), 2–2.65(m,13H), 3.94–4.05(m,1H), 5.32(m,1H), 7.22(d, 1H), 7.79(d,2H), 8. 18 (d, 1H).

EXAMPLE 21a

5-{((E)1S,5S,6S,7R)-7-Hydroxy-6-[(E/Z)-3-(4-nitrophenyl)-ureidoiminomethyl]-bicyclo[3.3.0]oct-3-ylidene}-pentanoic acid methyl ester 81 mg (232 micromol) of the compound produced according to example 1c is reacted analogously to example 1b with use of 4-(4-nitrophenyl)-semicarbazide hydrochloride and, after working up and purification, 21 mg (47 micromol, 20%) of the title compound is isolated as colorless oil.

IR (film): 3600–3000, 3340, 3220, 3120, 2940, 1725, 1690, 1600, 1540, 1505, 1415, 1330, 1230, 1175, 1110, 995, 850 and 735 cm$^{-1}$.

EXAMPLE 22

5-{((Z)-1S,5S,6S,7R)-7-Hydroxy-6-[(E/Z)-3-(4-nitrophenyl)-ureidoiminomethyl]-bicyclo[3.3.0]oct-3-ylidene}-pentanoic acid 60 mg (135 micromol) of the compound produced according to example 22a is saponified analogously to example 1 and, after working up and purification, 37 mg (85 micromol, 63%) of the title compound is isolated as pale yellow oil.

IR (film): 3600–2400, 3350, 3210, 2940, 1700, 1600, 1540, 1505, 1410, 1330, 1240, 1180, 1110, 850 and 735 cm$^{-1}$.

EXAMPLE 22a

5-{((Z)-1S,5S,6S,7R)-7-Hydroxy-6-[(E/Z)-3-(4-nitrophenyl)-ureidoiminomethyl]-bicyclo[3.3.0]oct-3-ylidene}-pentanoic acid methyl ester 100 mg (226 micromol) of the compound produced according to example 2c is reacted analogously to example 1b with use of 4-(4-nitrophenyl)-semicarbazide hydrochloride and, after working up and purification, 60 mg (135 micromol, 60%) of the title compound is isolated as pale yellow oil.

IR (film): 3600–3000, 3340, 3210, 3120, 2940, 1720, 1690, 1600, 1540, 1505, 1415, 1330, 1235, 1175, 1110, 995, 850 and 735 cm$^{-1}$.

EXAMPLE 23

5-{((E)-1S,5S,6S,7R)-7-Hydroxy-6-[(E/Z)-3-phenylthioureidoiminomethyl]-bicyclo[3.3.0]oct-3-ylidene}-pentanoic acid 52 mg (125 micromol) of the compound produced according to example 23a is saponified analogously to example 1 and, after working up and purification, 16 mg (40 micromol, 32%) of the title compound is isolated as colorless oil.

IR (CHCl$_3$): 3600–2400, 3410, 3330, 2950, 2860, 1710, 1595, 1530, 1495, 1430, 1315, 1250, 1180, 1125, 1075, 1030, 970 and 695 cm$^{-1}$.

EXAMPLE 23a

5-{((E)-1S,5S,6S,7R)-7-Hydroxy-6-[(E/Z)-3-phenylthioureidoiminomethyl]-bicyclo[3.3.0]oct-3-ylidene}-pentanoic acid methyl ester 111 mg (222 micromol) of the compound produced according to example 1c is reacted analogously to example 1a and, after working up and purification, 52 mg (125 micromol, 56%) of the title compound is isolated as colorless oil.

IR (film): 3600–3050, 3420, 3340, 3000, 2950, 2860, 1725, 1600, 1530, 1495, 1430, 1315, 1250, 1180, 1125, 1075, 1030, 970 and 695 cm$^{-1}$.

EXAMPLE 23b

5-{((E)-1S,5S,6S,7R)-7-(Tetrahydropyran-2-yloxy)-6-[(E/Z)-3-phenylthioureidoiminomethyl]-bicyclo[3.3.0]oct-3-ylidene}-pentanoic acid methyl ester 122 mg (350 micromol) of the compound produced according to example 1c is reacted analogously to example 1b with use of 4-phenyl-3-thiosemicarbazide and, after working up and purification, 111 mg (222 micromol, 63%) of the title compound is isolated as colorless oil.

IR (CHCl$_3$): 3420, 3340, 3000, 2950, 2860, 1725, 1595, 1530, 1495, 1430, 1315, 1250, 1180, 1125, 1075, 1030, 970, 870, 810 and 695 cm$^{-1}$.

EXAMPLE 24

5-{((Z)-1S,5S,6S,7R)-7-Hydroxy-6-[(E/Z)-3-phenylthioureidoiminomethyl]-bicyclo[3.3.0]oct-3-ylidene}-pentanoic acid 67 mg (161 micromol) of the compound produced according to example 24a is saponified analogously to example 1 and, after working up and purification, 31 mg (78 micromol, 48%) of the title compound is isolated as colorless solid.

IR (CHCl$_3$): 3600–2600, 3330, 2940, 1705, 1595, 1535, 1445, 1320, 1260, 1070, 1040, 930 and 670 cm$^{-1}$.

EXAMPLE 24a

5-{((Z)-1S,5S,6S,7R)-7-Hydroxy-6-[(E/Z)-3-phenylthioureidoiminomethyl]-bicyclo[3.3.0]oct-3-ylidene}-pentanoic acid methyl ester 100 mg (226 micromol) of the compound produced according to example 2c is reacted analogously to example 1b with use of 4-phenylthiosemicarbazide and with the addition of an equivalent p-toluenesulfonic acid and, after working up and purification, 67 mg (161 micromol, 71%) of the title compound is isolated as pale yellow oil.

IR (film): 3600–3000, 3310, 3040, 2940, 1725, 1595, 1530, 1495, 1430, 1310, 1255, 1195, 1080, 935, 750, 735 and 695 cm$^{-1}$.

EXAMPLE 25

5-{((E)-1S,5S,6S,7R)-7-Hydroxy-6-[(E/Z)-3-(2-chlorophenyl)-ureidoiminomethyl]-bicyclo[3.3.0]oct-3-ylidene}-pentanoic acid 69 mg (159 micromol) of the compound produced according to example 25a is saponified analogously to example 1 and, after working up and purification, 40 mg (95 micromol, 60%) of the title compound is isolated as colorless oil.

$^1$H-NMR (CD$_3$OD): δ=1.2–1.34(m, 1H), 1.6–1.74(m, 2H), 2–2.6(m,13H), 3.93–4.05(m, 1H), 5.32(m, 1H), 7.02 (dt,1H), 7.22–7.34(m,2H), 7.41(dd,1H), 8.2(dd, 1H).

EXAMPLE 25a

5-{((E)-1S,5S,6S,7R)-7-Hydroxy-6-[(E/Z)-3-(2-chlorophenyl)-ureidoiminomethyl]-bicyclo[3.3.0]oct-3-ylidene}-pentanoic acid methyl ester 81 mg (232 micromol) of the compound produced according to example 1c is reacted analogously to example 1b with use of 4-(2-chlorophenyl)-semicarbazide hydrochloride and, after working up and purification, 69 mg (159 micromol, 69%) of the title compound is isolated as colorless oil.

IR (film): 3600–3000, 3340, 3210, 3120, 2940, 1730, 1705, 1695, 1590, 1580, 1530, 1440, 1305, 1230, 1125, 1035, 935 and 750 cm$^{-1}$.

EXAMPLE 26

5-{((Z)-1S,5S,6S,7R)-7-Hydroxy-6-[(E/Z)-3-(2-chlorophenyl)-ureidoiminomethyl]-bicyclo[3.3.0]oct-3-ylidene}-pentanoic acid 114 mg (263 micromol) of the compound produced according to example 26a is saponified analogously to example 1 and, after working up and purification, 98 mg (232 micromol, 88%) of the title compound is isolated as colorless solid.

IR (KBr): 3600–2400, 3340, 3210, 3120, 2940, 1700, 1580, 1530, 1440, 1300, 1225, 1125, 1035, 935 and 750 cm$^{-1}$.

EXAMPLE 26a

5-{((Z)-1S,5S,6S,7R)-7-Hydroxy-6-[(E/Z)-3-(2-chlorophenyl)-ureidoiminomethyl]-bicyclo[3.3.0]oct-3-ylidene}-pentanoic acid methyl ester 125 mg (282 micromol) of the compound produced according to example 2c is reacted analogously to example 1b with use of 4-(2-chlorophenyl)-semicarbazide hydrochloride and, after working up and purification, 114 mg (263 micromol, 93%) of the title compound is isolated as colorless oil.

IR (film): 3600–3000, 3340, 3210, 3120, 2940, 1730, 1705, 1690, 1590, 1580, 1530, 1440, 1305, 1230, 1125, 1035, 935 and 750 cm$^{-1}$.

EXAMPLE 27

5-{((E)-1S,5S,6S,7R)-7-Hydroxy-6-[(E/Z)-3-(4-phenoxyphenyl)-thioureidoiminomethyl]-bicyclo [3.3.0]oct-3-ylidene}-pentanoic acid 71 mg (171 micromol) of the compound produced according to example 27a is saponified analogously to example 1 and, after working up and purification, 26 mg (53 micromol, 31%) of the title compound is isolated as colorless oil.

IR (film): 3600–2400, 3320, 3140, 3040, 2940, 2860, 1710, 1590, 1550–1450, 1435, 1400, 1280–1150, 1125, 1070, 1025, 970, 870, 840, 735 and 695 cm$^{-1}$.

EXAMPLE 27a

5-{(E)-1S,5S,6S,7R)-7-Hydroxy-6-[(E/Z)-3-(4-phenoxyphenyl)-thioureidoiminomethyl]-bicyclo [3.3.0]oct-3-ylidene}-pentanoic acid methyl ester 132 mg (223 micromol) of the compound produced according to example 27b is reacted analogously to example 1b and, after working up and purification, 71 mg (171 micromol, 77%) of the title compound is isolated as colorless oil.

IR (film): 3600–3000, 3330, 3140, 3040, 2940, 2860, 1730, 1590, 1550–1470, 1290–1150, 1125, 1070, 1025, 970, 840, 735 and 695 cm$^{-1}$.

EXAMPLE 27b

5-{((E)-1S,5S,6S,7R)-7-(Tetrahydropyran-2-yloxy)-6-[(E/Z)-3-(4-phenoxyphenyl)-thioureidoiminomethyl]-bicyclo[3.3.0.]oct-3-ylidene}-pentanoic acid methyl ester 122 mg (350 micromol) of the compound produced according to example 1c is reacted analogously to example 1b with use of 4-(4-phenoxyphenyl)-semicarbazide and, after working up and purification, 132 mg (223 micromol, 64%) of the title compound is isolated as colorless oil.

IR (film): 3320, 3130, 3040, 2940, 2850, 1730, 1590, 1550 1470, 1270–1150, 1125, 1070, 1025, 970, 870, 840, 810, 735 and cm$^{-1}$.

EXAMPLE 28

5-{((Z)-1S,5S,6S,7R)-7-Hydroxy-6-[(E/Z)-3-(4-phenoxyphenyl)-thioureidoiminomethyl]-bicyclo [3.3.0]oct-3-ylidene}-pentanoic acid 60 mg (118 micromol) of the compound produced according to example 28a is saponified analogously to example 1 and, after working up and purification, 17 mg (35 micromol, 30%) of the title compound is isolated as colorless oil.

IR (film): 3600–2400, 3320, 3050, 2940, 1700, 1590, 1540, 1500, 1480, 1400, 1310, 1225, 1165, 1070, 870, 845, 740 and 690 cm$^{-1}$.

EXAMPLE 28a

5-{((Z)-1S,5S,6S,7R)-7-Hydroxy-6-[(E/Z)-3-(4-phenoxyphenyl)-thioureidoiminomethyl]-bicyclo [3.3.0]oct-3-ylidene}-pentanoic acid methyl ester 125 mg (282 micromol) of the compound produced according to example 2c is reacted analogously to example 1b with use of 4-(4-phenoxyphenyl)-semicarbazide hydrochloride and, after working up and purification, 60 mg (118 micromol, 42%) of the title compound is isolated as pale yellow oil.

IR (film): 3600–3100, 3320, 3050, 2940, 1725, 1590, 1540, 1500, 1485, 1400, 1310, 1230, 1165, 1070, 870, 845, 740 and 690 cm$^{-1}$.

EXAMPLE 29

5-{((Z)-1S,5S,6S)-6-[(E/Z)-3-phenylureidoiminomethyl]-bicyclo[3.3.0]oct-3-ylidene}-pentanoic acid 85 mg (227 micromol) of the compound produced according to example 29a is saponified analogously to example 1 and, after working up and purification, 65 mg (176 micromol, 77%) of the title compound is isolated as crystalline solid.

$^1$ H-NMR (CD$_3$OD): δ=1.25–1.48(m, 1H), 1.5–1.74(m, 3H), 1.85–2.6(m,13H), 5.2–5.3(m, 1H), 7.05(t,1H), 7.2(d, 1H), 7.28(t,1H), 7.48(d,1H).

EXAMPLE 29a

5-{((Z)-1S,5S,6S)-6-[(E/Z)-3-phenylureidoiminomethyl]-bicyclo[3.3.0]oct-3-ylidene}-pentanoic acid methyl ester 67 mg (267 micromol) of the compound produced according to example 29b is reacted analogously to example 1b with use of 4-phenylsemicarbazide and, after working up and purification, 87 mg (227 micromol, 85%) of the title compound is isolated as colorless oil.

IR (film): 3370, 3200, 3100, 2940, 2860, 1735, 1685, 1590, 1530, 1445, 1310, 1230, 1195, 1170, 1130, 755 and 690 cm$^{-1}$.

EXAMPLE 29b

5-{((Z)-1S,5S,6S)-6-Formyl-bicyclo[3.3.0]oct-3-ylidene}-pentanoic acid methyl ester 273 mg (1.08 mmol) of the compound produced according to example 29c is oxidized analogously to example 1c and, after working up, 275 mg of the title compound is isolated as colorless oil, which is further reacted without purification.

EXAMPLE 29c

5-{((Z)-1S,5S,6S)-6-Hydroxymethyl-bicyclo[3.3.0] oct-3-ylidene}-pentanoic acid methyl ester 531 mg (1.08 mmol) of the compound produced according to example 29d is reacted analogously to example 1d and, after working up and purification, 273 mg (1.08 mmol, 100%) of the title compound is isolated as colorless oil.

IR (film): 3600–3200, 2940, 2860, 1735, 1435, 1245, 1225, 1170 and 1030 cm$^{-1}$.

EXAMPLE 29d

5-{((Z)-1S,5S,6S)-6-tert-Butyldiphenylsilyloxymethyl-bicyclo[3.3.0]oct-3-ylidene}-pentanoic acid methyl ester 755 mg (1.14 mmol) of the tosylate produced according to example 29e is dissolved in 10 ml of dimethoxyethane, mixed with 760 mg of zinc dust, 880 mg of sodium iodide, 670 microliters of water and refluxed for 9 hours. After cooling, it is filtered, washed with diethyl ether and the combined organic phases are washed with 10% sodium thiosulfate solution, water and saturated sodium chloride solution and dried on magnesium sulfate. The title compound (531 mg, 1.08 mmol, 95%) obtained after filtration and removal of the solvent is further reacted without purification.

IR (film): 3070, 3040, 2940, 2850, 1735, 1590, 1425, 1245, 1165, 1110, 820, 740 and 700 cm$^{-1}$.

EXAMPLE 29e

5-{((Z)-1S,5S,6S,7R)-7-(Toluenesulfonyloxy)-6-tert-butyldiphenylsilyloxymethyl-bicyclo[3.3.0]oct-3-ylidene}-pentanoic acid methyl ester 600 mg (1.18 mmol) of the alcohol produced according to example 29f is dissolved in 2 ml of anhydrous pyridine, mixed with the solution of 936 mg of p-toluenesulfonic acid chloride in 2 ml of anhydrous pyridine and heated for 2 hours under an atmosphere of dry argon to 55° C. After cooling, it is poured on a 2 n hydrochloric acid, extracted with diethyl ether, the combined organic extracts are washed with water and saturated sodium chloride solution and dried on magnesium sulfate. The residue obtained after filtration and removal of the solvent is purified by chromatography on about 100 ml of fine silica gel with use of a gradient system of n-hexane and ethyl acetate. 755 mg (1.14 mmol, 97%) of the title compound is isolated as colorless oil.

IR (film): 3070, 3040, 2940, 2850, 1735, 1600, 1425, 1360, 1190, 1175, 1110, 960, 935, 860, 820, 740, 705 and 665 cm$^{-1}$.

EXAMPLE 29f

5-{((Z)-1S,5S,6S,7R)-7-Hydroxy-6-tert-butyldiphenylsilyloxymethyl-bicyclo[3.3.0]oct-3-ylidene}-pentanoic acid methyl ester 997 mg (1.69 mmol) of the compound produced according to example 2e is reacted analogously to example 1a and, after working up and purification, 863 mg (1.69 mmol, 100%) of the title compound is isolated as colorless oil.

IR (film): 3600–3200, 3070, 3050, 2940, 2850, 2735, 1590, 1425, 1240, 1110, 820, 740 and 705 cm$^{-1}$.

EXAMPLE 30

5-{((Z)-1S,5S,6S)-6-[(E/Z)-3-(4-Chlorophenyl)-ureidoiminomethyl]-bicyclo[3.3.0]oct-3-ylidene}-pentanoic acid 62 mg (148 micromol) of the compound produced according to example 30a is saponified analogously to example 1 and, after working up and purification, 45 mg (112 micromol, 72%) of the title compound is isolated as crystalline solid.

$^1$H-NMR (CD$_3$OD): δ=1.24–1.38(m, 1H), 1.5–1.74(m, 3H), 1.85–2.6(m,13H), 5.2–5.3(m, 1H), 7.19(d,1H), 7.27(d, 2H), 7.51(d,2H).

EXAMPLE 30a

5-{((Z)-1S,5S,6S)-6-[(E/Z)-3-(4-Chlorophenyl)-ureidoiminomethyl]-bicyclo[3.3.0]oct-3-ylidene}-pentanoic acid methyl ester 67 mg (267 micromol) of the compound produced according to example 29b is reacted analogously to example 1b with use of 4-(4-chlorophenyl)-semicarbazide hydrochloride and, after working up and purification, 65 mg (156 micromol, 58%) of the title compound is isolated as colorless oil.

IR (film): 3360, 3200, 3200, 2940, 2860, 1730, 1685, 1590, 1525, 1490, 1435, 1400, 1310, 1280, 1230, 1170, 1130, 1090, 1010, 870, 825 and 745 cm$^{-1}$.

EXAMPLE 31

5-{((Z)-1S,5S,6S)-6-[(E/Z)-3-(3,4-Dichlorophenyl)-ureidoiminomethyl]-bicyclo[3.3.0]oct-3-ylidene}-pentanoic acid 87 mg (192 micromol) of the compound produced according to example 31a is saponified analogously to example 1 and, after working up and purification, 71 mg (163 micromol, 85%) of the title compound is isolated as crystalline solid.

$^1$H-NMR (CD$_3$OD): δ=1.25–1.38(m, 1H), 1.5–1.74(m, 3H), 1.85–2.6(m,13H), 5.2–5.3(m, 1H), 7.19(d,1H), 7.41(m, 2H), 7.9(m, 1H).

EXAMPLE 31a

5-{((Z)-1S,5S,6S)-6-[(E/Z)-3-(3,4-Dichlorophenyl)-ureidoiminomethyl]-bicyclo[3.3.0]oct-3-ylidene}-pentanoic acid methyl ester 67 mg (267 micromol) of the compound produced according to example 29b is reacted analogously to example 1b with use of 4-(3,4-dichlorophenyl)-semicarbazide hydrochloride and, after working up and purification, 87 mg (192 micromol, 72%) of the title compound is isolated as colorless oil.

IR (film): 3360, 3200, 3110, 2940, 2860, 1730, 1690, 1575, 1520, 1475, 1390, 1295, 1225, 1195, 1170, 1130, 1025, 875, 815, 745 and 690 cm$^{-1}$.

EXAMPLE 32

5-{((Z)-1S,5S,6S)-6-[(E/Z)-3-(4-Nitrophenyl)-ureidoiminomethyl]-bicyclo[3.3.0]oct-3-ylidene}-pentanoic acid 98 mg (229 micromol) of the compound produced according to example 32a is saponified analogously to example 1 and, after working up and purification, 84 mg (203 micromol, 87%) of the title compound is isolated as crystalline solid.

$^1$H-NMR (CD$_3$OD): δ=1.25–1.4(m, 1H), 1.5–1.74(m, 3H), 1.87–2.6(m,13H), 5.2–5.3(m, 1H), 7.22(d,1H), 7.8(d, 2H), 8.19(d,2H).

EXAMPLE 32a

5-{((Z)-1S,5S,6S)-6-[(E/Z)-3-(4-Nitrophenyl)-ureidoiminomethyl]-bicyclo[3.3.0]oct-3-ylidene}-pentanoic acid methyl ester 67 mg (267 micromol) of the compound produced according to example 29b is reacted analogously to example 1b with use of 4-(4-nitrophenyl)-semicarbazide hydrochloride and, after working up and purification, 100 mg (233 micromol, 87%) of the title compound is isolated as colorless oil.

IR (film): 3340, 3200, 3110, 2940, 2860, 1725, 1690, 1600, 1535, 1505, 1410, 1330, 1235, 1175, 1110, 995, 850, 750 and 690 cm$^{-1}$.

EXAMPLE 33

5-{((E)-1S,5S,6S)-6-[(E/Z)-3-Phenylureidoiminomethyl]-bicyclo[3.3.0]oct-3-ylidene}-pentanoic acid 52 mg (136 micromol) of the compound produced according to example 33a is saponified analogously to example 1 and, after working up and purification, 29 mg (78 micromol, 58%) of the title compound is isolated as colorless oil.

$^1$H-NMR (CD$_3$OD): δ=1.25–1.4(m,2H), 1.5–1.72(m,3H), 1.85–2.7(m,12H), 5.2–5.3(m,1H), 7.04(t,1H), 7.18(d,1H), 7.29(t,2H), 7.47(d,2H).

EXAMPLE 33a

5-{((E)-1S,5S,6S)-6-[(E/Z)-3-phenylureidoiminomethyl]-bicyclo[3.3.0]oct-3-ylidene}-pentanoic acid methyl ester 50 mg (200 micromol) of the compound produced according to example 33b is reacted analogously to example 1b and, after working up and purification, 52 mg (136 micromol, 68%) of the title compound is isolated as colorless oil.

IR (film): 3370, 3200, 3100, 2940, 2860, 1730, 1685, 1595, 1530, 1445, 1315, 1230, 1170, 1130, 755, 735 and 695 cm$^{-1}$.

EXAMPLE 33b

5-{((E)-1S,5S,6S)-6-Formyl-bicyclo[3.3.0]oct-3-ylidene}-pentanoic acid methyl ester 456 mg (1.81 mmol) of the compound produced according to example 33c is reacted analogously to example 1c and, after working up and purification, 458 mg of the title compound, which is further reacted without purification, is isolated as colorless oil.

EXAMPLE 33c

5-{((E)-1S,5S,6S)-6-Hydroxymethyl-bicyclo[3.3.0]oct-3-ylidene}-pentanoic acid methyl ester 895 mg (1.82 mmol) of the compound produced according to example 33d is reacted analogously to example 1d and, after working up and purification, 456 mg (1.81 mmol, 99%) of the title compound is isolated as colorless oil.

IR (film): 3600–3100, 2940, 2850, 1735, 1435, 1245, 1225, 1170 and 1030 cm$^{-1}$.

EXAMPLE 33d

5-{((E)-1S,5S,6S)-6-tert-Butyldiphenylsilyloxymethyl-bicyclo[3.3.0]oct-3-ylidene}-pentanoic acid methyl ester 1.28 g (1.94 mmol) of the compound produced according to example 33e is reacted analogously to example 29d and, after working up and purification, 895 mg (1.82 mmol, 94%) of the title compound is isolated as colorless oil.

IR (film): 3070, 3050, 2940, 2950, 1740, 1590, 1425, 1245, 1165, 1110, 820, 740 and 700 cm$^{-1}$.

EXAMPLE 33e

5-{((E)-1S,5S,6S,7R)-7-(Toluenesulfonyloxy)-6-tert-butyldiphenylsilyloxymethyl-bicyclo[3.3.0]oct-3-ylidene}-pentanoic acid methyl ester 1.05 g (2.06 mmol) of the compound produced according to example 33f is reacted analogously to example 29e and, after working up and purification, 1.28 g (1.94 mmol, 94%) of the title compound is isolated as colorless oil.

IR (film): 3070, 3050, 2940, 2850, 1735, 1595, 1425, 1360, 1185, 1175, 1110, 960, 940, 840, 815, 740, 700 and 665 cm$^{-1}$.

EXAMPLE 33f

5-{((E)-1S,5S,6S,7R)-7-Hydroxy-6-tert-butyldiphenylsilyloxymethyl-bicyclo[3.3.0]oct-3-ylidene}-pentanoic acid methyl ester 3.84 g (6.37 mmol) of the compound produced according to example 1e is reacted analogously to example 1a and, after working up and purification, 2.98 g (5.88 mmol, 92%) of the title compound is isolated as colorless oil.

IR (film): 3600–3100, 3070, 3050, 2940, 2850, 1735, 1590, 1425, 1245, 1170, 1110, 820, 740 and 705 cm$^{-1}$.

EXAMPLE 34

5-{((E)-1S,5S,6S)-6-[(E/Z)-3-(4-Chlorophenyl)-ureidoiminomethyl]-bicyclo[3.3.0]oct-3-ylidene}-pentanoic acid 35 mg (123 micromol) of the compound produced according to example 34a is saponified analogously to example 1 and, after working up and purification, 17 mg (42 micromol, 34%) of the title compound is isolated as colorless oil.

$^1$H-NMR (CDCl$_3$): δ=1.4–2.88(m,17H), 5.25–5.35(m, 1H), 6.43(d,0.7H), 7.08(d,0.3H), 7.26(d,2H), 7.44(d,2H), 8.02(s,NH), 8.24(s,NH), 9.08(s,NH), 10.4(s,NH).

EXAMPLE 34a

5-{((E)-1S,5S,6S)-6-[(E/Z)-3-(4-Chlorophenyl)-ureidoiminomethyl]-bicyclo[3.3.0]oct-3-ylidene}-pentanoic acid methyl ester 50 mg (200 micromol) of the compound produced according to example 33b is reacted analogously to example 1b with use of 4-(4-chlorophenyl)-semicarbazide hydrochloride and, after working up and purification, 35 mg (123 micromol, 62%) of the title compound is isolated as colorless oil.

IR (film): 3370, 3200, 3100, 2940, 2860, 1725, 1685, 1590, 1525, 1490, 1405, 1310, 1230, 1175, 1125, 1090, 825 and 735 cm$^{-1}$.

EXAMPLE 35

5-{((E)-1S,5S,6S)-6-[(E/Z)-3-(3,4-Dichlorophenyl)-ureidoiminomethyl]-bicyclo[3.3.0]oct-3-ylidene}-pentanoic acid 44 mg (138 micromol) of the compound produced according to example 35a is saponified analogously to example 1 and, after working up and purification, 22 mg (50 micromol, 36%) of the title compound is isolated as colorless oil.

$^1$H-NMR (CDCl$_3$): δ=1.4–2.86(m,17H), 5.25–5.35(m, 1H), 6.45(d,0.7H), 7.08(d,0.3H), 7.34(m,2H), 7.72(m, 1H), 8.05(s,NH), 8.28(s,NH), 9.13(s,NH), 10.43(s,NH).

EXAMPLE 35a

5-{((E)-1S,5S,6S)-6-[(E/Z)-3-(3,4-Dichlorophenyl)-ureidoiminomethyl]-bicyclo[3.3.0]oct-3-ylidene}-pentanoic acid methyl ester 50 mg (200 micromol) of the compound produced according to example 33b is reacted analogously to example 1b with use of 4-(3,4-dichlorophenyl)-semicarbazide hydrochloride and, after working up and purification, 44 mg (138 micromol, 69%) of the title compound is isolated as colorless oil.

IR (film): 3370, 3200, 3110, 2940, 2860, 1725, 1690, 1580, 1520, 1475, 1390, 1295, 1260, 1130, 1025, 875, 810, 735 and 705 cm$^{-1}$.

EXAMPLE 36

5-{((E)-1S,5S,6S)-6-[(E/Z)-3-(4-Nitrophenyl)-ureidoiminomethyl]-bicyclo[3.3.0]oct-3-ylidene}-pentanoic acid 26 mg (61 micromol) of the compound produced according to example 36a is saponified analogously to example 1 and, after working up and purification, 12 mg (29 micromol, 47%) of the title compound is isolated as colorless oil.

$^1$H-NMR (CDCl$_3$): δ=1.45–2.88 (m, 17H), 5.25–5.35 (m, 1H), 6.5(d,0.65H), 7.12(d,0.35H), 7.68(d,2H), 8.2(m,2H), 8.41(s,NH), 8.63(s,NH), 9.23(s,NH), 10.54(s,NH).

EXAMPLE 36a

5-{((E)-1S,5S,6S)-6-[(E/Z)-3-(4-Nitrophenyl)-ureidoiminomethyl]-bicyclo[3.3.0]oct-3-ylidene}-pentanoic acid methyl ester 50 mg (200 micromol) of the compound produced according to example 33b is reacted analogously to example 1b with use of 4-(4-nitrophenyl)-semicarbazide hydrochloride and, after working up and purification, 26 mg (61 micromol, 31%) of the title compound is isolated as colorless oil.

IR (film): 3350, 3200, 3110, 2940, 2860, 1725, 1695, 1600, 1535, 1505, 1410, 1330, 1235, 1175, 1110, 855 and 750 cm$^{-1}$.

EXAMPLE 37

5-{((E)-1S,5S,6S)-6-[(E/Z)-3-(3-Chlorophenyl)-ureidoiminomethyl]-bicyclo[3.3.0]oct-3-ylidene}-pentanoic acid 34 mg (119 micromol) of the compound produced according to example 37a is saponified analogously to example 1 and, after working up and purification, 18 mg (45 micromol, 37%) of the title compound is isolated as colorless oil.

$^1$H-NMR (CDCl$_3$): δ=1.4–2.86 (m, 17H), 5.25–5.35 (m, 1H), 6.45(d,0.7H), 7.0–7.08(m, 1H), 7.09(d,0.3H), 7.19–7.27(m,1H), 7.3–7.37(m,1H), 7.62(m, 1H), 8.03(s, NH), 8.26(s,NH), 9.15(s,NH), 10.4(s,NH).

EXAMPLE 37a

5-{((E)-1S,5S,6S)-6-[(E/Z)-3-(3-Chlorophenyl)-ureidoiminomethyl]bicyclo[3.3.0]oct3ylidene}-pentanoic acid methyl ester 50 mg (200 micromol) of the compound produced according to example 33b is reacted analogously to example 1b with use of 4-(3-chlorophenyl)-semicarbazide hydrochloride and, after working up and purification, 34 mg (119 micromol, 60%) of the title compound is isolated as colorless oil.

IR (film): 3360, 3200, 3100, 2940, 2860, 1725, 1685, 1585, 1525, 1480, 1425, 1300, 1225, 1170, 1125, 1010, 875, 775, 745 and 680 cm$^{-1}$.

EXAMPLE 38

4-{((E)-1S,5S,6S,7R)-7-Hydroxy-6-[(E/Z)-3-phenylureidoiminomethyl]-bicyclo[3.3.0]oct-3-ylidene}-butanoic acid 35 mg (91 micromol) of the compound produced according to example 38a is saponified analogously to example 1 and, after working up and purification, 21 mg (55 micromol, 61%) of the title compound is isolated as colorless oil.

$^1$H-NMR (CDCl$_3$): δ=1.2–1.45(m,1H), 1.95–2.77(m, 13H), 3.9–4.03(m,1H), 5.2–5.35(m,1H), 5.4–6.6(1H, COOH), 6.48(d,0.35H), 7.02(t,1H), 7.09(d,0.65H), 7.2–7.55 (m,4H), 8.16(s,NH), 8.22(s,NH), 9.8(s,NH), 9.95(s,NH).

EXAMPLE 38a

4-{((E)-1S,5S,6S,7R)-7-Hydroxy-6-[(E/Z)-3-phenylureidoiminomethyl]-bicyclo[3.3.0]oct-3-ylidene}-butanoic acid methyl ester The solution of 80 mg (238 micromol) of the aldehyde, produced according to example 38b, in 2 ml of anhydrous ethanol is mixed with 48 mg of 4-phenylsemicarbazide, 18 mg of pyridinium-p-toluenesulfonate and heated for 6 hours under an atmosphere of dry argon to 55° C. The working up takes place as described in example 1a. After purification, 56 mg (145 micromol, 61%) of the title compound is isolated as colorless oil.

IR (film): 3600–3100, 3360, 3100, 2940, 2850, 1730, 1680, 1590, 1530, 1445, 1325, 1230, 1175, 1130, 1030, 940, 755 and 690 cm$^{-1}$.

EXAMPLE 38b

4-{((E)-1S,5S,6R,7R)-7-(Tetrahydropyran-2-yloxy)-6-formyl-bicyclo[3.3.0]oct-3-ylidene}-butanoic acid methyl ester 600 mg (1.77 mmol) of the compound produced according to example 38c is reacted analogously to example 1c and, after working up, 607 mg of the title compound is isolated as colorless oil, which is further reacted without purification.

EXAMPLE 38c

4-{((E)-1S,5S,6S,7R)-7-(Tetrahydropyran-2-yloxy)-6-hydroxymethyl-bicyclo[3.3.0]oct-3-ylidene}-butanoic acid methyl ester 4.11 g (7.3 mmol) of the compound produced according to example 38d is reacted analogously to example 1d and, after working up and purification, 2.36 g (6.97 mmol, 96%) of the title compound is isolated as colorless oil.

IR (film): 3600–3200, 2940, 2860, 1735, 1435, 1350, 1255, 1200, 1170, 1135, 1075, 1020, 975, 865 and 810 cm$^{-1}$.

EXAMPLE 38d

4-{((E)-1S,5S,6S,7R)-7-(Tetrahydropyran-2-yloxy)-6-tert-butyldiphenylsilyloxymethyl-bicyclo[3.3.0]oct-3-ylidene}-butanoic acid methyl ester 9.54 mg (17 mmol) of compound A produced according to example 38e is reacted analogously to example 1e and, after working up and purification, 8.39 g (14.5 mmol, 86%) of the title compound is isolated as colorless oil.

IR (film): 3070, 3050, 2940, 2850, 1740, 1425, 1350, 1255, 1130, 1110, 1075, 1035, 1020, 975, 820, 740 and 705 cm$^{-1}$.

EXAMPLE 38e

4-{((E)-1S,5S,6S,7R)-7-(Tetrahydropyran-2-yloxy)-6-tert-butyldiphenylsilyloxymethyl-bicyclo[3.3.0]oct-3-ylidene}-butanoic acid (A) and 4-{((Z)-1S,5S,6S,7R)-7-(tetrahydropyran-2-yloxy)-6-tert-butyldiphenylsilyloxymethyl-bicyclo[3.3.0]oct-3-ylidene}-butanoic acid (B)

19.1 g (38.8 mmol) of the compound produced according to example 1g is reacted analogously to example 1f and, after working up and purification, 9.54 g (17 mmol, 44%) of title compound A, 5.57 g (9.9 mmol, 26%) of title compound B as well as 3.78 g (6.72 mmol, 17%) of a mixed fraction of A and B are each isolated as colorless oil.

IR (film) of A and B: 3600–2400, 3070, 3050, 3010, 2940, 2850, 1705, 1425, 1355, 1200, 1125, 1110, 1075, 1020, 865, 815, 740 and 695 cm$^{-1}$.

EXAMPLE 39

4-{((Z)-1S,5S,6S,7R)-7-Hydroxy-6-[(E/Z)-3-phenylureidoiminomethyl]-bicyclo[3.3.0]oct-3-ylidene}-butanoic acid 54 mg (140 micromol) of the compound produced according to example 39a is saponified analogously to example 1 and, after working up and purification, 25 mg (67 micromol, 48%) of the title compound is isolated as colorless solid.

$^1$H-NMR (CD$_3$OD): δ=1.2–1.32(m, 1H), 1.98–2.57(m, 13H), 3.98(m,1H), 5.28–5.36(m, 1H), 7.03(t,1H), 7.22(d, 1H), 7.28(t,2H), 7.49(d,2H).

EXAMPLE 39a

4-{((Z)-1S,5S,6S,7R)-7-Hydroxy-6-[(E/Z)-3-phenylureidoiminomethyl]-bicyclo[3.3.0]oct-3-ylidene}-butanoic acid methyl ester 120 mg (358 micromol) of the compound produced according to example 39b is reacted analogously to example 38a and, after working up and purification, 54 mg (140 micromol, 39%) of the title compound is isolated as colorless oil.

IR (film): 3600–3000, 3360, 3210, 3100, 2940, 2840, 1725, 1680, 1590, 1530, 1445, 1320, 1230, 1170, 1130, 755, 735 and 690 cm$^{-1}$.

EXAMPLE 39b

4-{((Z)-1S,5S,6R,7R)-7-(Tetrahydropyran-2-yloxy)-6-formyl-bicyclo[3.3.0]oct-3-ylidene}-butanoic acid methyl ester 600 mg (1.77 mmol) of the compound produced according to example 39c is reacted analogously to example 1c and, after working up, 602 mg of the title compound is isolated as colorless oil, which is further reacted without purification.

EXAMPLE 39c

4-{((Z)-1S,5S,6S,7R)-7-(Tetrahydropyran-2-yloxy)-6-hydroxymethyl-bicyclo[3.3.0]oct-3-ylidene}-butanoic acid methyl ester 2.63 g (4.67 mmol) of the compound produced according to example 39d is reacted analogously to example 1d and, after working up and purification, 1.58 g (4.67 mmol, 100%) of the title compound is isolated as colorless oil.

IR (film): 3600–3100, 2940, 2860, 1735, 1435, 1350, 1255, 1200, 1165, 1130, 1075, 1020 and 975 cm$^{-1}$.

EXAMPLE 39d

4-{((Z)-1S,5S,6S,7R)-7-(Tetrahydropyran-2-yloxy)-6-tert-butyldiphenylsilyloxymethyl-bicyclo[3.3.0]oct-3-ylidene}-butanoic acid methyl ester 5.57 g (9.9 mmol) of compound B produced according to example 38e is reacted analogously to example 1e and, after working up and purification, 5.1 g (8.84 mmol, 89%) of the title compound is isolated as colorless oil.

IR (film): 3070, 3040, 2940, 2850, 1740, 1425, 1350, 1255, 1110, 1075, 1035, 1020, 870, 820, 740 and 700 cm$^{-1}$.

EXAMPLE 40

4-{((E)-1S,5S,6S,7R)-7-Hydroxy-6-[(E/Z)-3-(3-chlorophenyl)-ureidoiminomethyl]-bicyclo[3.3.0]oct-3-ylidene}-butanoic acid 131 mg (311 micromol) of the compound produced according to example 40a is saponified analogously to example 1 and, after working up and purification, 46 mg (113 micromol, 36%) of the title compound is isolated as colorless solid.

$^1$H-NMR (CD$_3$OD): δ=1.2–1.34 (m, 1H), 2.05–2.65 (m, 13H), 3.93–4.04(m, 1H), 5.33(m,1H), 7.03(m, 1H), 7.2(d, 1H), 7.25(t,1H), 7.71(m, 1H).

EXAMPLE 40a

4-{((E)-1S,5S,6S,7R)-7-Hydroxy-6-[(E/Z)-3-(3-chlorophenyl)-ureidoiminomethyl]-bicyclo[3.3.0]oct-3-ylidene}-butanoic acid methyl ester 128 mg (355 micromol) of the compound produced according to example 38b is reacted analogously to example 38a with use of 4-(3-chlorophenyl)-semicarbazide hydrochloride and, after working up and purification, 131 mg (311 micromol, 88%) of the title compound is isolated as colorless solid.

IR (CHCl$_3$): 3380, 2950, 1725, 1690, 1590, 1530, 1480, 1430, 1300, 1220, 1095, 1075, 1010, 930, 875 and 670 cm$^{-1}$.

EXAMPLE 41

4-{((Z)-1S,5S,6S,7R)-7-Hydroxy-6-[(E/Z)-3-(3-chlorophenyl)-ureidoiminomethyl]-bicyclo[3.3.0]oct-3-ylidene}-butanoic acid 86 mg (171 micromol) of the compound produced according to example 41a is saponified analogously to example 1 and, after working up and purification, 37 mg (91 micromol, 53%) of the title compound is isolated as colorless solid.

$^1$H-NMR (CD$_3$OD): δ=1.2–1.34(m, 1H), 2.0–2.56(m, 13H), 3.93–4.04(m, 1H), 5.31(m,1H), 7.03(m,1H), 7.22(d, 1H), 7.25(t,1H), 7.38 (m, 1H), 7.72 (m, 1H).

EXAMPLE 41a

4-{((Z)-1S,5S,6S,7R)-7-Hydroxy-6-[(E/Z)-3-(3-chlorophenyl)-ureidoiminomethyl]-bicyclo[3.3.0]oct-3-ylidene}-butanoic acid methyl ester 120 mg (358 micromol) of the compound produced according to example 39b is reacted analogously to example 38a with use of 4-(3-chlorophenyl)-semicarbazide hydrochloride and, after working up and purification, 86 mg (171 micromol, 48%) of the title compound is isolated as colorless oil.

IR (film): 3600–3000, 3360, 3210, 3110, 2940, 2840, 1725, 1680, 1585, 1530, 1480, 1430, 1300, 1260, 1230, 1190, 1170, 1130, 1095, 1075, 1010, 870, 775, 735 and 680 cm$^{-1}$.

EXAMPLE 42

4-{((E)-1S,5S,6S,7R)-7-Hydroxy-6-[(E/Z)-3-(4-chlorophenyl)-ureidoiminomethyl]-bicyclo[3.3.0]oct-3-ylidene}-butanoic acid 118 mg (281 micromol) of the compound produced according to example 42a is saponified analogously to example 1 and, after working up and purification, 44 mg (108 micromol, 39%) of the title compound is isolated as colorless solid.

$^1$H-NMR (CD$_3$OD): δ=1.2–1.34(m,1H), 2.05–2.6(m, 13H), 3.93–4.04(m, 1H), 5.32(m,1H), 7.2(d,1H), 7.27(d, 2H), 7.52(d,2H).

EXAMPLE 42a

4-{((E)-1S,5S,6S,7R)-7-Hydroxy-6-[(E/Z)-3-(4-chlorophenyl)-ureidoiminomethyl]-bicyclo[3.3.0]oct-3-ylidene}-butanoic acid methyl ester 128 mg (355 micromol) of the compound produced according to example 38b is reacted analogously to example 38a with use of 4-(4-chlorophenyl)-semicarbazide hydrochloride and, after working up and purification, 118 mg (281 micromol, 79%) of the title compound is isolated as colorless solid.

IR (CHCl$_3$): 3600–3000, 3380, 3200, 3100, 2950, 1725, 1685, 1590, 1530, 1490, 1435, 1405, 1310, 1220, 1175, 1125, 1090, 1010, 935 and 825 cm$^{-1}$.

EXAMPLE 43

4-{((Z)-1S,5S,6S,7R)-7-Hydroxy-6-[(E/Z)-3-(4-chlorophenyl)-ureidoiminomethyl]-bicyclo[3.3.0]oct-3-ylidene}-butanoic acid 83 mg (165 micromol) of the compound produced according to example 43a is saponified analogously to example 1 and, after working up and purification, 42 mg (103 micromol, 63%) of the title compound is isolated as colorless solid.

$^1$H-NMR (CD$_3$OD): δ=1.2–1.34 (m, 1H), 1.95–2.55 (m, 13H), 3.93–4.04 (m, 1H), 5.33 (m, 1H), 7.22 (d, 1H), 7.27 (d, 2H), 7.52 (d, 2H).

EXAMPLE 43a

4-{((Z)-1S,5S,6S,7R)-7-Hydroxy-6-[(E/Z)-3-(4-chlorophenyl)-ureidoiminomethyl]-bicyclo[3.3.0]oct-3-ylidene}-butanoic acid methyl ester 120 mg (358 micromol) of the compound produced according to example 39b is reacted analogously to example 38a with use of 4-(4-chlorophenyl)-semicarbazide hydrochloride and, after working up and purification, 83 mg (165 micromol, 46%) of the title compound is isolated as colorless oil.

IR (film): 3600–3000, 3360, 3110, 2940, 2840, 1725, 1680, 1590, 1530, 1490, 1405, 1310, 1230, 1175, 1125, 1090, 1010, 825 and 740 cm$^{-1}$.

EXAMPLE 44

4-{((E)-1S,5S,6S,7R)-7-Hydroxy-6-[(E/Z)-3-(3,4-dichlorophenyl)-ureidoiminomethyl]-bicyclo[3.3.0]oct-3-ylidene}-butanoic acid 119 mg (262 micromol) of the compound produced according to example 44a is saponified analogously to example 1 and, after working up and purification, 39 mg (89 micromol, 34%) of the title compound is isolated as colorless solid.

$^1$H-NMR (CD$_3$OD): δ=1.2–1.34(m, 1H), 2.05–2.65(m, 13H), 3.93–4.03(m, 1H), 5.33(m, 1H), 7.2(d,1H), 7.42(m, 2H), 7.88(m, 1H).

EXAMPLE 44a

4-{((E)-1S,5S,6S,7R)-7-Hydroxy-6-[(E/Z)-3-(3,4-dichlorophenyl)-ureidoiminomethyl]-bicyclo[3.3.0]oct-3-ylidene}-butanoic acid methyl ester 128 mg (355 micromol) of the compound produced according to example 38b is reacted analogously to example 38a with use of 4-(3,4-dichlorophenyl)-semicarbazide hydrochloride and, after working up and purification, 119 mg (262 micromol, 74%) of the title compound is isolated as colorless solid.

IR (KBr): 3370, 3200, 3110, 2940, 2840, 1735, 1690, 1580, 1530, 1475, 1395, 1300, 1190, 1165, 1120, 1025, 940, 875, 810 and 745 cm$^{-1}$.

EXAMPLE 45

4-{((Z)-1S,5S,6S,7R)-7-Hydroxy-6-[(E/Z)-3-(3,4-dichlorophenyl)-ureidoiminomethyl]-bicyclo[3.3.0]oct-3-ylidene}-butanoic acid 95 mg (176 micromol) of the compound produced according to example 45a is saponified analogously to example 1 and, after working up and purification, 46 mg (104 micromol, 59%) of the title compound is isolated as colorless solid.

$^1$H-NMR (CD$_3$OD): δ=1.2–1.34(m, 1H), 1.95–2.6(m, 13H), 3.94–4.04(m, 1H), 5.31(m, 1H), 7.22(d,1H), 7.42(m, 2H), 7.89(m, 1H).

EXAMPLE 45a

4-{((Z)-1S,5S,6S,7R)-7-Hydroxy-6-[(E/Z)-3-(3,4-dichlorophenyl)-ureidoiminomethyl]-bicyclo[3.3.0]oct-3-ylidene}-butanoic acid methyl ester 120 mg (358 micromol) of the compound produced according to example 39b is reacted analogously to example 38a with use of 4-(3,4-dichlorophenyl)-semicarbazide hydrochloride and, after working up and purification, 95 mg (176 micromol, 49%) of the title compound is isolated as colorless oil.

IR (film): 3600–3000, 3360, 3200, 3110, 2940, 2840, 1730, 1690, 1580, 1530, 1475, 1395, 1295, 1265, 1175, 1120, 1025, 935, 875, 810 and 740 cm$^{-1}$.

EXAMPLE 46

4-{((E)-1S,5S,6S,7R)-7-Hydroxy-6-[(E/Z)-3-(4-nitrophenyl)-ureidoiminomethyl]-bicyclo[3.3.0]oct-3-ylidene}-butanoic acid 123 mg (286 micromol) of the compound produced according to example 46a is saponified analogously to example 1 and, after working up and purification, 27 mg (65 micromol, 23%) of the title compound is isolated as colorless solid.

$^1$H-NMR (CD$_3$OD): δ=1.2–1.33(m,1H), 2.05–2.6(m, 13H), 3.93–4.04(m, 1H), 5.33(m, 1H), 7.22(d,1H), 7.8(d, 2H), 8.2(d,2H).

EXAMPLE 46a

4-{((E)-1S,5S,6S,7R)-7-Hydroxy-6-[(E/Z)-3-(4-nitrophenyl)-ureidoiminomethyl]-bicyclo[3.3.0]oct-3-ylidene}-butanoic acid methyl ester 128 mg (355 micromol) of the compound produced according to example 38b is reacted analogously to example 38a with use of 4-(4-nitrophenyl)-semicarbazide hydrochloride and, after working up and purification, 123 mg (286 micromol, 81%) of the title compound is isolated as colorless solid.

IR (CHCl$_3$): 3600–3000, 3360, 3210, 2950, 1720, 1695, 1600, 1535, 1510, 1415, 1335, 1220, 1175, 1110 and 850 cm$^{-1}$.

EXAMPLE 47

4-{((Z)-1S,5S,6S,7R)-7-Hydroxy-6-[(E/Z)-3-(4-nitrophenyl)-ureidoiminomethyl]-bicyclo[3.3.0]oct-3-ylidene}-butanoic acid 93 mg (181 micromol) of the compound produced according to example 47a is saponified analogously to example 1 and, after working up and purification, 36 mg (86 micromol, 48%) of the title compound is isolated as colorless solid.

$^1$H-NMR (CD$_3$OD): δ=1.2–1.32(m, 1H), 1.98–2.58(m, 13H), 3.98(m, 1H), 5.32(m, 1H), 7.24(d, 1H), 7.8(d,2H), 8.18(d,2H).

EXAMPLE 47a

4-{((Z)-1S,5S,6S,7R)-7-Hydroxy-6-[(E/Z)-3-(4-nitrophenyl)-ureidoiminomethyl]-bicyclo[3.3.0]oct-3-ylidene}-butanoic acid methyl ester 120 mg (358 micromol) of the compound produced according to example 39b is reacted analogously to example 38a with use of 4-(4-nitrophenyl)-semicarbazide hydrochloride and, after working up and purification, 93 mg (181 micromol, 51%) of the title compound is isolated as colorless oil.

IR (film): 3600–3000, 3340, 3110, 2940, 2840, 1720, 1705, 1690, 1600, 1540, 1505, 1415, 1330, 1235, 1175, 1110, 1000, 850 and 735 cm$^{-1}$.

EXAMPLE 48

5-{((Z)-1S,5S,6S,7R)-7-Hydroxy-6-[(E/Z)-2-(2,4,5-trichlorophenylsulfonyl)-hydrazonomethyl]-bicyclo[3.3.0]oct-3-ylidene}-pentanoic acid 56 mg (107 micromol) of the compound produced according to example 48a is saponified analogously to example 1 and, after working up and purification, 30 mg (59 micromol, 55%) of the title compound is isolated as colorless oil.

$^1$H-NMR (CD$_3$OD): δ=1.1–1.21(m, 1H), 1.52–2.54(m, 14H), 3.8–3.9(m, 1H), 5.18–5.25(m, 1H), 7.29(d,1H), 7.88 (m, 1H), 8.20(m, 1H).

EXAMPLE 48a

5-{((Z)-1S,5S,6S,7R)-7-Hydroxy-6-[(E/Z)-2-(2,4,5-trichlorophenylsulfonyl)-hydrazonomethyl]-bicyclo[3.3.0]oct-3-ylidene}-pentanoic acid methyl ester The solution of 99 mg (283 micromol) of the aldehyde, produced according to example 2c, in 2.5 ml of anhydrous ethanol is mixed with 106 mg of 2,4,5-trichlorophenylsulfonic acid hydrazide and stirred for 1.5 hours at 55° C. under an atmosphere of dry argon. Then, it is mixed with a spatula tip full of pyridinium-p-toluenesulfonate and heated for another 2 hours to 55° C. The residue obtained after removal of the solvent is purified by chromatography on 7 analytic thin-layer slabs. A mixture of n-hexane and ethyl acetate is used as mobile solvent, trichloromethane and ethanol are used as eluant. 56 mg (107 micromol, 38%) of the title compound is isolated as colorless oil.

IR (film): 3600–3100, 3200, 3090, 2840, 1730, 1710, 1440, 1365, 1325, 1170, 1065, 870, 735, 690, 660 and 625 cm$^{-1}$.

EXAMPLE 49

5-{((Z)-1S,5S,6S,7R)-7-Hydroxy-6-[(E/Z)-2-(4-methoxyphenylsulfonyl)-hydrazonomethyl]-bicyclo[3.3.0]oct-3-ylidene}-pentanoic acid 87 mg (193 micromol) of the compound produced according to example 49a is saponified analogously to example 1 and, after working up and purification, 44 mg (101 micromol, 52%) of the title compound is isolated as colorless oil.

$^1$H-NMR (CD$_3$OD): δ=1.13–1.26 (m, 1H), 1.6–1.72 (m, 2H), 1.9–2.55(m,12H), 3.8–3.9(m, 1H), 3.87(s,3H), 5.18–5.29(m, 1H), 7.07(d,2H), 7.18(d,1H), 7.81(d,2H).

EXAMPLE 49a

5-{((Z)-1S,5S,6S,7R)-7-Hydroxy-6-[(E/Z)-2-(4-methoxyphenylsulfonyl)-hydrazonomethyl]-bicyclo[3.3.0]oct-3-ylidene}-pentanoic acid methyl ester 99 mg (283 micromol) of the compound produced according to example 2c is reacted analogously to example 48a with use of (4-methoxyphenyl)sulfonic acid hydrazide and, after working up and purification, 87 mg (193 micromol, 68%) of the title compound is isolated as colorless oil.

IR (film): 3600–3000, 3200, 2940, 2840, 1735, 1595, 1495, 1435, 1350, 1320, 1260, 1155, 1095, 1020, 935, 835, 800, 735 and 675 cm$^{-1}$.

EXAMPLE 50

5-{((Z)-1S,5S,6S,7R)-7-Hydroxy-6-[(E/Z)-2-(4-fluorophenylsulfonyl)-hydrazonomethyl]-bicyclo[3.3.0]oct-3-ylidene}-pentanoic acid 50 mg (114 micromol) of the compound produced according to example 50a is saponified analogously to example 1 and, after working up and purification, 27 mg (64 micromol, 56%) of the title compound is isolated as colorless oil.

$^1$H-NMR (CD$_3$OD): δ=1.13–1.25(m, 1H), 1.6–1.73(m, 2H), 1.9–2.55 (m, 12H), 3.8–3.9 (m, 1H), 5.2–5.3 (m, 1H), 7.18 (d, 1H), 7.24–7.34 (m, 2H), 7.88–7.98 (m, 2H).

EXAMPLE 50a

5-{((Z)-1S,5S,6S,7R)-7-Hydroxy-6-[(E/Z)-2-(4-fluorophenylsulfonyl)-hydrazonomethyl]-bicyclo[3.3.0]oct-3-ylidene}-pentanoic acid methyl ester 99 mg (283 micromol) of the compound produced according to example 2c is reacted analogously to example 48a with use of (4-fluorophenyl)-sulfonic acid hydrazide and, after working up and purification, 50 mg (114 micromol, 40%) of the title compound is isolated as colorless oil.

IR (film): 3600–3250, 3200, 3060, 2940, 1730, 1590, 1490, 1435, 1355, 1320, 1265, 1240, 1170, 1155, 1090, 840, 735, 700 and 670 cm$^{-1}$.

EXAMPLE 51

5-{((Z)-1S,5S,6S,7R)-7-Hydroxy-6-[(E/Z)-2-(4-methylphenylsulfonyl)-hydrazonomethyl]-bicyclo[3.3.0]oct-3-ylidene}-pentanoic acid 69 mg (159 micromol) of the compound produced according to example 51a is saponified analogously to example 1 and, after working up and purification, 32 mg (76 micromol, 48%) of the title compound is isolated as colorless oil.

$^1$H-NMR (CD$_3$OD): δ=1.12–1.24 (m, 1H), 1.6–1.73 (m, 2H), 1.88–2.54(m,12H), 2.42(s,3H), 3.8–3.9(m,1H), 5.2–5.29(m, 1H), 7.17 (d, 1H), 7.38 (d, 2H), 7.76 (m, 2H).

EXAMPLE 51a

5-{((Z)-1S,5S,6S,7R)-7-Hydroxy-6-[(E/Z)-2-(4-methylphenylsulfonyl)-hydrazonomethyl]-bicyclo[3.3.0]oct-3-ylidene}-pentanoic acid methyl ester 69 mg (197 micromol) of the compound produced according to example 2c is reacted analogously to example 48a with use of toluenesulfonic acid hydrazide and, after working up and purification, 69 mg (159 micromol, 81%) of the title compound is isolated as colorless oil.

IR (CHCl$_3$): 3600–3300, 3180, 3000, 2950, 2860, 1725, 1595, 1435, 1355, 1325, 1255, 1165, 1090, 1035, 1020, 810 and 660 cm$^{-1}$.

EXAMPLE 52

5-{((Z)-1S,5S,6S,7R)-7-Hydroxy-6-[(E/Z)-2-(phenylsulfonyl)-hydrazonomethyl]-bicyclo[3.3.0]oct-3-ylidene}-pentanoic acid 59 mg (140 micromol) of the compound produced according to example 52a is saponified analogously to example 1 and, after working up and purification, 30 mg (74 micromol, 53%) of the title compound is isolated as colorless oil.

$^1$H-NMR (CD$_3$OD): δ=1.12–1.25 (m, 1H), 1.6–1.72 (m, 2H), 1.88–2.54(m,12H), 3.79–3.9(m, 1H), 5.2–5.28(m, 1H), 7.17(d,1H), 7.52–7.68 (m, 3H), 7.85–7.93 (m, 2H).

EXAMPLE 52a

5-{((Z)-1S,5S,6S,7R)-7-Hydroxy-6-[(E/Z)-2-(phenylsulfonyl)-hydrazonomethyl]-bicyclo[3.3.0]oct-3-ylidene}-pentanoic acid methyl ester 69 mg (197 micromol) of the compound produced according to example 2c is reacted analogously to example 48a with use of benzenesulfonic acid hydrazide and, after working up and purification, 59 mg (140 micromol, 71%) of the title compound is isolated as colorless oil.

IR (CHCl$_3$): 3600–3300, 3200, 3000, 2950, 1725, 1630, 1445, 1360, 1320, 1260, 1165, 1090, 1015, 810 and 685 cm$^{-1}$.

We claim:
1. A bicyclo[3.3.0]octane compound of formula I,

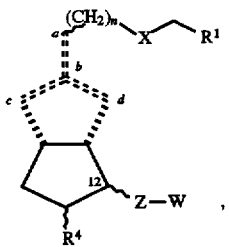

and enantiomers thereof, in which at most one double bond lies between the carbon atoms of centers a-b or b-c or b-d, R$^1$ is —COOR$^5$ and R$^5$ is hydrogen or C$_1$-C$_{10}$ alkyl, C$_3$-C$_{10}$ cycloalkyl, C$_7$-C$_{16}$ aralkyl, each optionally substituted by halogen, phenyl, C$_1$-C$_4$ alkoxy or di-(C$_1$-C$_4$) alkoxy or di-(C$_1$-C$_4$)-alkylamino; phenacyl or C$_6$-C$_{12}$ aryl substituted by Y; a 5- or 6-membered heterocyclic radical with at least one N, O or S atom; or —CONHR$_7$ wherein R$^7$ is hydrogen, C$_1$-C$_{10}$ alkanoyl or C$_1$-C$_{10}$ alkanesulfonyl, X is a CH$_2$ group or an O or S atom, n is 0–2, R$^4$ is a hydrogen atom, a free or functionally modified hydroxy group in the α- or β-position, Z is 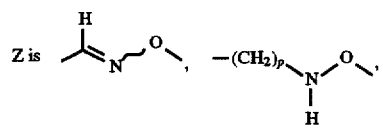

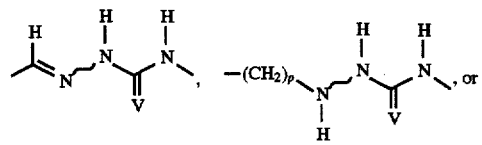

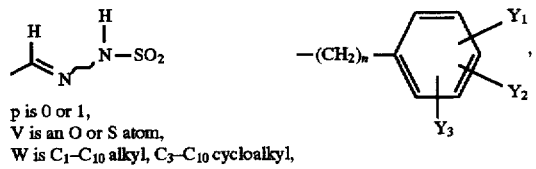

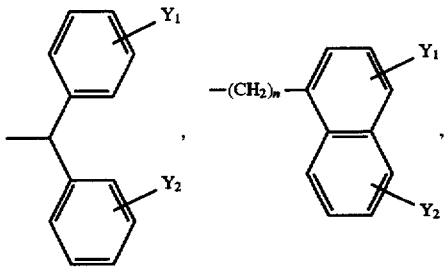

p is 0 or 1,
V is an O or S atom,
W is C$_1$-C$_{10}$ alkyl, C$_3$-C$_{10}$ cycloalkyl,

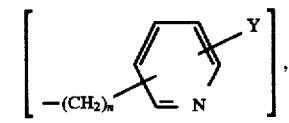

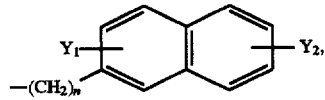

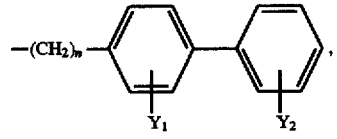

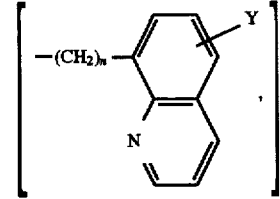

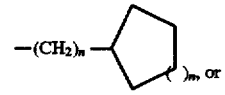

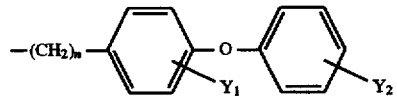

substituted by Y,
Y$_1$, Y$_2$ and Y$_3$ are the same or different and have the meaning given for Y,
Y is hydrogen, halogen, N$_3$, CF$_3$, OR$^6$, NO$_2$, COOR$^6$ or C$_1$-C$_{10}$ alkyl, $R^6$ is hydrogen, $C_1-C_{10}$ alkyl, $C_6-C_{12}$ aryl or $C_7-C_{16}$ aralkyl optionally substituted by halogen and, if $R^5$ is hydrogen, their salts with physiologically compatible bases, and α-, β- or γ-cyclodextrin clathrates of the compounds of formula I.

2. The compound of claim 1, which is an α-, β- or γ-cyclodextrin clathrate of a compound of formula I.

3. A compound of claim 1, wherein X is a $CH_2$ group or an O atom.

4. A composition of a bicyclo[3.3.0]octane compound of formula I, encapsulated with liposomes;

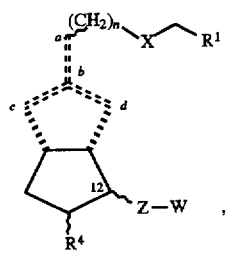

(I)

and enantiomers thereof, in which at most one double bond lies between the carbon atoms of centers a-b or b-c or b-d, $R^1$ is $-COOR^5$ and $R^5$ is hydrogen or $C_1-C_{10}$ alkyl, $C_3-C_{10}$ cycloalkyl, $C_7-C_{16}$ aralkyl, each optionally substituted by halogen, phenyl, $C_1-C_4$ alkoxy or di-$(C_1-C_4)$ alkoxy or di-$(C_1-C_4)$-alkylamino; phenacyl or $C_6-C_{12}$ aryl substituted by Y; a 5- or 6-membered heterocyclic radical with at least one N, O or S atom; or $-CONHR_7$ wherein $R^7$ is hydrogen, $C_1-C_{10}$ alkanoyl or $C_1-C_{10}$ alkanesulfonyl, X is a $CH_2$ group or an O or S atom, n is 0–2, $R^4$ is a hydrogen atom, a free or functionally modified hydroxy group in the α- or β-position, Z is 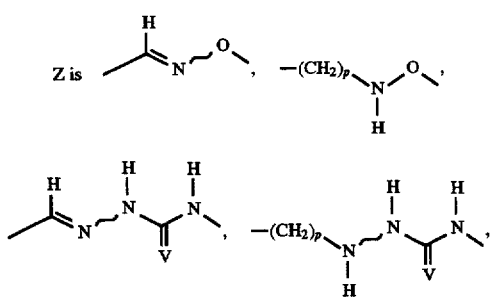

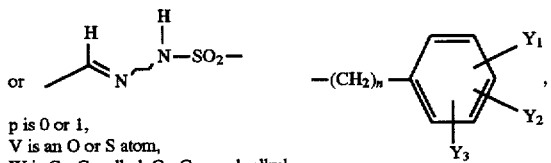

p is 0 or 1,
V is an O or S atom,
W is $C_1-C_{10}$ alkyl, $C_3-C_{10}$ cycloalkyl,

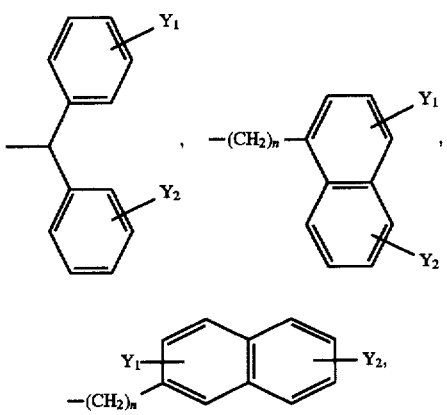

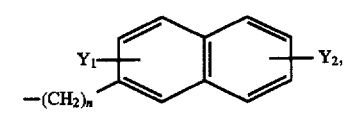

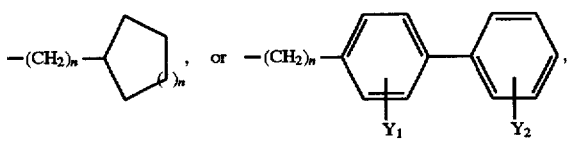

substituted by Y, $Y_1$, $Y_2$ and $Y_3$ are the same or different have the meaning given for Y, Y is hydrogen, halogen, $N_3$, $CF_3$, $OR^6$, $NO_2$, $COOR^6$ or $C_1-C_{10}$ alkyl, $R^6$ is hydrogen, $C_1-C_{10}$ alkyl, $C_6-C_{12}$ aryl or $C_7-C_{16}$ aralkyl optionally substituted by halogen and, if $R^5$ is hydrogen, their salts with physiologically compatible bases.

5. Auxiliary agents for pharmacological studies and pharmaceutical agents of one or more compounds of formula I of claim 4 and usual auxiliary agents, vehicles and additives.

6. Auxiliary agents for pharmacological studies and pharmacological agents of one or more compounds of claim 2, and usual auxiliary agents, vehicles or additives.

* * * * *